(12) United States Patent
Detamore et al.

(10) Patent No.: US 12,377,191 B2
(45) Date of Patent: Aug. 5, 2025

(54) CHONDROINDUCTIVE PEPTIDES AND COMPOSITIONS AND METHODS OF USE THEREOF

(71) Applicant: The Board of Regents of the University of Oklahoma, Norman, OK (US)

(72) Inventors: Michael S. Detamore, Norman, OK (US); Salma Mahzoon, Eldridge, MD (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 839 days.

(21) Appl. No.: 17/271,339

(22) PCT Filed: Aug. 28, 2019

(86) PCT No.: PCT/US2019/048604
§ 371 (c)(1),
(2) Date: Feb. 25, 2021

(87) PCT Pub. No.: WO2020/047123
PCT Pub. Date: Mar. 5, 2020

(65) Prior Publication Data
US 2021/0346573 A1 Nov. 11, 2021

Related U.S. Application Data

(60) Provisional application No. 62/723,674, filed on Aug. 28, 2018.

(51) Int. Cl.
| | | |
|---|---|---|
| *A61L 27/26* | (2006.01) | |
| *A61K 38/08* | (2019.01) | |
| *A61K 47/61* | (2017.01) | |
| *A61K 47/65* | (2017.01) | |
| *A61L 27/22* | (2006.01) | |
| *A61L 27/52* | (2006.01) | |
| *C07K 14/00* | (2006.01) | |

(52) U.S. Cl.
CPC ............ *A61L 27/26* (2013.01); *A61K 38/08* (2013.01); *A61K 47/61* (2017.08); *A61K 47/65* (2017.08); *A61L 27/227* (2013.01); *A61L 27/52* (2013.01); *C07K 14/00* (2013.01); *A61L 2300/25* (2013.01); *A61L 2300/412* (2013.01); *A61L 2300/622* (2013.01); *A61L 2430/06* (2013.01)

(58) Field of Classification Search
CPC .. A61L 27/227; A61L 27/52; A61L 2300/412; A61L 2430/06; A61L 2300/622
See application file for complete search history.

(56) References Cited

U.S. PATENT DOCUMENTS

| | | | |
|---|---|---|---|
| 6,756,215 B1 | 6/2004 | Wolfraim et al. | |
| 2005/0177118 A1 | 8/2005 | Hoganson et al. | |
| 2010/0061962 A1* | 3/2010 | Li | A61L 27/56 424/93.7 |
| 2011/0123592 A1* | 5/2011 | Stevens | A61L 27/38 424/78.17 |
| 2016/0159937 A1 | 6/2016 | Auzely et al. | |
| 2017/0275653 A1* | 9/2017 | Bomble | C12N 9/1022 |

FOREIGN PATENT DOCUMENTS

| | | | | |
|---|---|---|---|---|
| WO | WO-9940114 A1 * | 8/1999 | ....... | C07K 14/70571 |
| WO | WO 01/85762 A2 * | 11/2001 | ............... | C07K 7/06 |
| WO | 2016115345 A1 | 7/2016 | | |

OTHER PUBLICATIONS

Betts et al., Bioinformatics for Geneticists, Chapter 14: Amino Acid Properties and Consequences of Substitutions, 2003, pp. 289-316.. (Year: 2003).*
Adessi et al., Current Medicinal Chemistry, 2002, vol. 9. pp. 963-978.. (Year: 2002).*
Dimova et al., Future Science OA, 2018, vol. 4(2) pp. 1-18.. (Year: 2018).*
Studysmarter, "Polymer", StudySmarter, available online at https://www.studysmarter.co.uk/explanations/biology/biological-molecules/monomers-and-polymers/, 19 pages, (accesed on Feb. 19, 2024),. (Year: 2022).*
Bian et al., Biomaterials, vol. 32 (2011), pp. 6425-6434. (Year: 2011).*
Mergy et al., Journal of Polymer Science Part A: Polymer Chemistry, 2012, vol. 50, pp. 4019-4028.. (Year: 2012).*
Karel et al., Carbohydrate Polymers, vol. 201 (2018), pp. 300-307.. (Year: 2018).*
Munger, J. S., et al.; "Interactions between growth factors and integrins: latent forms of transforming growth factor-beta are ligands for the integrin alphavbeta1"; Mol Biol Cell; 9:2627-38 (1998).
Munger, J. S., et al.; "The integrin alpha v beta 6 binds and activates latent TGF beta 1: a mechanism for regulating pulmonary inflammation and fibrosis"; Cell; 96:319-28 (1999).
Verrecchio, A., et al.; "Design of peptides with high affinities for heparin and endothelial cell proteoglycans"; Journal of Biological Chemistry; 275:7701-7707 (2000).
Barry, F., et al.; "Chondrogenic differentiation of mesenchymal stem cells from bone marrow: differentiation-dependent gene expression of matrix components"; Exp Cell Res; 26/:189-200 (2001).

(Continued)

*Primary Examiner* — Lianko G Garyu
*Assistant Examiner* — Claudia Espinosa
(74) *Attorney, Agent, or Firm* — Hall Estill Law Firm

(57) ABSTRACT

Compositions and peptides for enhancing formation of cartilage in a site of a cartilage injury or defect, or joint condition, and methods of the use of the compositions and peptides in such treatments. Examples of the sites may include a knee, ankle, wrist, shoulder, elbow, patella, hip, vertebrae, femoral head, temporomandibular joint, glenoid of the scapula, jaw, and growth plate.

16 Claims, 12 Drawing Sheets

Specification includes a Sequence Listing.

(56) References Cited

OTHER PUBLICATIONS

Makagiansar, I. T., et al.; "Improving the selectivity of HAV-peptidesd in modulating E-cadherin-E-cadherin interactions in the intercellular junction of MDCK cell monolayers"; Pharm Res; 18:446-53 (2001).
Mu, D., et al.; "The integrin alpha(v)beta8 mediates epithelial homeostasis through MT1-MMP-dependent activation of TGF-beta1"; J Cell Biol.; 157:493-507 (2002).
Sinaga, E., et al.; "Increasing paracellular porosity by E-cadherin peptides: discovery of bulge and groove regions in the EC1-domain of E-cadherin"; Pharm Res.; 19:1170-9 (2002).
Ludbrook, S. B., et al.; "The integrin alphavbeta3 is a receptor for the latency-associated peptides of transforming growth factos beta 1 and beta3"; Biochem J; 369:311-8 (2003).
Mwale, F., et al.; "A synthetic peptide of link protein stimulates the biosynthesis of collagens II, IX and proteoglycan by cells of the intervertebral disc"; J Cell Biochem; 88:1202-13 (2003).
French, M. M., et al.; "Chondrogenic differentiation of adult dermal fibroblasts" Ann Biomed Eng; 32:50-6 (2004).
Wang, G., et al.; "Rac1/Cdc42 and RhoA GTPases antagonistically regulate chondrocyte proliferation, hypertrophy, and apoptosis"; J Bone Miner Res; 20:1022-31 (2005).
Woods, A., et al.; "Rac1 signaling stimulates N-cadherin expression, mesenchymal condensation, and chondrogenesis"; J Biol Chem; 282:23500-8 (2007).
McAllister, T. N., et al.; "Cell-based therapeutics from an economic perspective: primed for a commercial success or a research sinkhole"; Regen Med; 3:925-37 (2008).
Embree, M. C., et al.; "Biglycan and fibromodulin have essential roles in regulating chondrogenesis and extracellular matrix turnover in temporomandibular joint osteoarthritis"; Am J Pathol; 176:812-26 (2010).
Liu, S. Q., et al.; "Biommetic hydrogels for chondrogenic differentiation of human mesenchymal stem cells to neocartilage"; Biomaterials; 31:7298-7307 (2010).
Mummery, C. L., et al.; "Challenges in using stem cells for cardiac repair"; Sci Transl Med; 2:27ps17 (2010).
Wojtowicz, A. M., et al.; "Coating of biomaterial scaffolds with the collagen-mimetic peptide GFOGER for bone defect repair"; Biomaterials; 31:2574-82 (2010).
Burdick, J. A., et al.; "Hyaluronic acid hydrogels for biomedical applications"; Adv Mater; 23:H41-56 (2011).
Ceylan, H., et al.; "Selective adhesion and growth of vasular endothelial cells on bioactive peptide nanofiber functionalized stainless steel surface"; Biomaterials; 32:8797-805 (2011).
Mwale, F., et al.; "The efficacy of Link N as a mediator of repair in a rabbit model of intervertebral disc degeneration"; Arthritis Res Ther; 13:R120 (2011).
Wei, Y., et al.; "Different complex surfaces of plyethyleneglycol (PEG) and REDV ligand to enhance the endothelial cells selectivity over smooth muscle cells"; Colloids Surf B Biointerfaces; 84:369-78 (2011).
Lin, X., et al.; "B2A peptide induces chondrogenic differentiation in vitro and enhances cartilage repair in rats"; Journal of Orthopaedic Research; 30:1221-1228 (2012).
Renner, J. N., et al.; "Bone Morphogenetic Protein-Derived Peptide Promotes Chondrogenic Differentiation of Human Mesenchymal Stem Cells"; Tissue Engineering Part A; 18:2581-2589 (2012).
Svensen, N., et al.; "Peptides for cell-selective drug delivery"; Trends Pharmacol Sci; 33:186-92 (2012).
Burdick, J. A., et al.; "Acellular biomaterials: an evolving alternative to cell-based therapies"; Sci Transl Med; 5:176ps4 (2013).
Caprini, A., et al.; "A novel bioactive peptide: assessing its activity over murine neural stem cells and its potential for neural tissue engineering"; N Biotechnol; 30:552-62 (2013).
Kim, I. L., et al.; "Fibrous hyaluronic acid hydrogels that direct MSC chondrogenesis through mechanical and adhesive cues"; Biomaterials; 34:5571-80 (2013).
Wei, Y., et al.; "Surface engineering of cardiovascular stent with endothelial cell selectivity for in vivo re-endothelialisation"; Biomaterials; 34:2588-99 (2013).
Xiao, Y., et al.; "Mechanical testing of hydrogels in cartilage tissue engineering: beyond the compressive modulus"; Tissue Eng Part B Rev; 19:403-12 (2013).
Gray, B. P., et al.; "Combinatorial peptide libraries: mining for cell-binding peptides"; Chem Rev; 114:1020-81 (2014).
Mahzoon, S., et al.; "Funtionalizing With Bioactive Peptides to Generate Bio-Instructive Scaffolds"; Bio-Instructive Scaffolds for Musculoskeletal Tissue Engineering and Regenerative Medicine; 37 (2016).
Moreno-Caceres, J., et al.; "Caveolin-1-dependent activation of the metalloprotease TACE/ADAM17 by TGF-beta in hepatocytes requires activation of Src and the NADPH oxidase NOX1"; FEBS J; 283:1300-10 (2016).
Detamore, M. S., et al.; "Chondroinductive Peptides: Drawing Inspiration from Cell-Matrix Interactions"; Tissue Eng Part B Rev (2018).
Townsend, J. M., et al.; "Superior calvarial bone regeneration using pentenoate-functionalized hyaluronic acid hydrogels with devitalized tendon particles"; Acta Biomater; 71:148-155 (2018).
PCT/US2019/048604; "International Search Report and Written Opinion"; Dec. 10, 2019; 15 pages.

\* cited by examiner

CHONDROINDUCTIVE PEPTIDES AND COMPOSITIONS AND METHODS OF USE THEREOF

CROSS REFERENCE TO RELATED APPLICATIONS

The present application is a national stage application of a PCT application having International Application No. PCT/US2019/048604, filed Aug. 18, 2019, which claims priority to U.S. Provisional Application having U.S. Ser. No. 62/723,674, filed Aug. 28, 2018, which claims the benefit under 35 U.S.C. 119 (e), the disclosure of which is hereby expressly incorporated herein by reference.

BACKGROUND

Cartilage tissue does not have the ability to regenerate on its own. Minor injury to cartilage tissue may therefore lead to further degeneration and eventually to arthritis, which is the leading cause of disability worldwide. The current surgical treatments for cartilage injury such as autologous chondrocyte implantation (ACI), microfracture, osteochondral transplantation (mosaicplasty), and allograft implants, do not reproducibly lead to tissue with the same mechanical and structural properties of native articular cartilage. The failure of current treatments to regenerate a fully integrated and effective cartilage tissue has motivated the regenerative medicine community to investigate strategies that lead to the creation of fully functional hyaline cartilage. Cell-based approaches may be promising in terms of hyaline cartilage formation, but inherent translational challenges motivate the identification of acellular alternatives. Acellular materials may support chondroinductivity if natural components such as extracellular matrix (ECM) molecules or growth factors are added to their structure. While natural components may mimic the native cartilage environment and be chondroinductive, their limitations (e.g., cost, reproducibility, and potential for immunogenicity or disease transmission) present challenges for commercial adoption. Therefore, an all-synthetic biomaterial, providing chondroinductive capabilities without the need for animal-derived components or cells, may offer a superior alternative. To regenerate cartilage tissue with an all-synthetic material, the ideal scaffolding biomaterial should have mechanical integrity suitable for weight-bearing application and the ability to induce chondrogenic differentiation of endogenous mesenchymal stem cells (MSCs). The desirable failure properties (e.g., maximum stress and strain, and toughness) of the material may be achieved via specific polymer composition; however, identifying all-synthetic cellular signals for chondroinduction is the remaining challenge. It is to address this challenge that the presently disclosed embodiments are directed.

DETAILED DESCRIPTION

Figure 1:
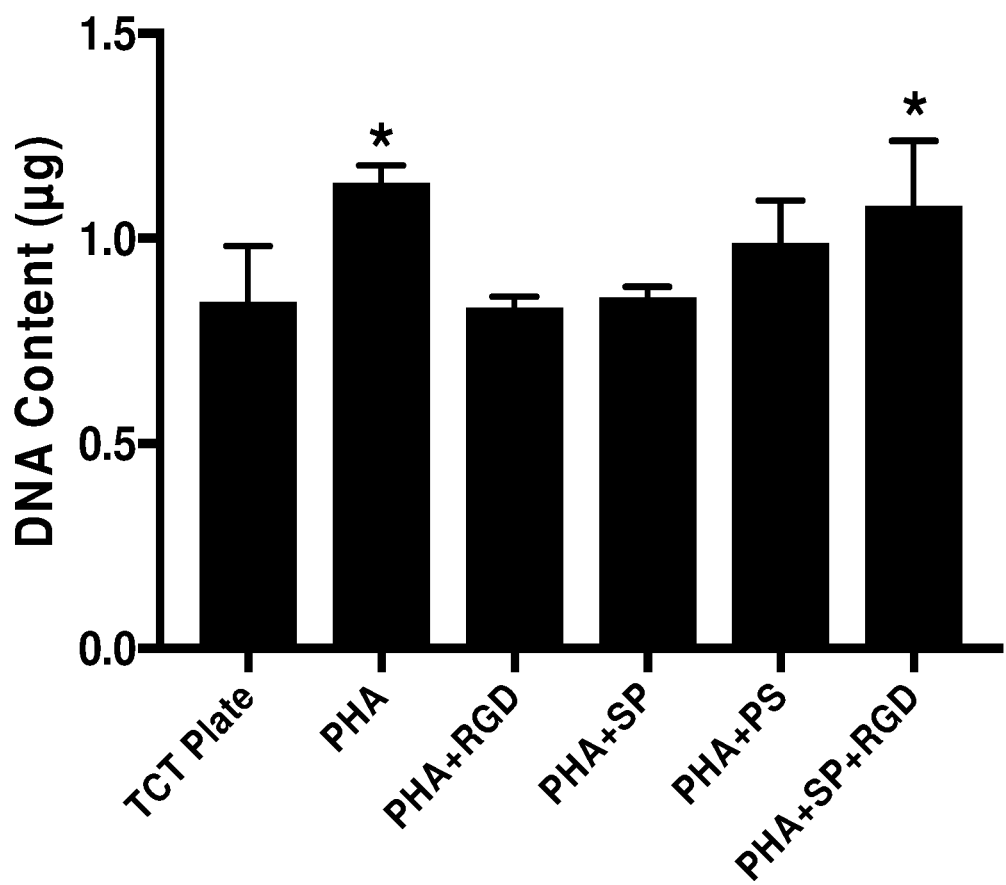
FIG. 1 shows the analysis of DNA content of rat bone marrow mesenchymal stem cells (rBMSCs) after 3 days of culture on hydrogel surfaces with various peptide compositions. Culture surfaces were Tissue Culture Treated (TCT) Plate (a control), pentanoate-functionalized hyaluronic acid (PHA) (a control), PHA+RGD: PHA+GCGYGRGDSP (SEQ ID NO:6), PHA+SP: PHA+GCGYGSPPEPS (SEQ ID NO:7), PHA+PS: PHA+GCGYGPSEPSP (SEQ ID NO:8), (a control), and PHA+SP+RGD): PHA+GCGYGSPPEPS+GCGYGRGDSP. (*)=p<0.05 compared to the TCT plate group (n=3).

Conventional medicine has no therapy that will regenerate hyaline cartilage. A biomaterial that is intrinsically chondroinductive would provide such a therapy. The present disclosure is therefore directed to, in at least certain embodiments, synthetic chondroinductive materials for use in regenerating hyaline cartilage. The synthetic materials comprise novel chondroinductive peptides conjugated to functionalized hyaluronic acid. In at least one embodiment, the chondroinductive peptide has the amino acid sequence Ser-Pro-Pro-Glu-Pro-Ser (SPPEPS—SEQ ID NO:2). In certain embodiments, the chondroinductive peptides can be used in a method to stimulate chondrogenic differentiation of stem cells, such as mesenchymal stem cells.

In humans, when articular cartilage fails to heal spontaneously, it leads to partial-thickness cartilage lesions that have fissures less than 1.5 cm in diameter. The exposed cell surfaces in the lesion cannot support cell adhesion, cell migration or fibrin clot attachment. When the fissures extend down to subchondral bone and have diameter greater than 1.5 cm, it is often categorized as full-thickness cartilage lesions. Full or partial thickness cartilage defects can affect any cartilaginous structure including the knee, elbow, wrist, ankle, shoulder and hip joints. Therefore, the method of treating partial-thickness cartilage lesions includes treating any cartilage defect, cartilage injury, or joint condition including those selected from the group of knee, elbow, wrist, ankle, shoulder and hip joints, or others as described elsewhere herein. In accordance with the present disclosure, the cartilage lesion can be treated for repair by implanting a chondroinductive scaffold composition as described herein. The chondroinductive scaffold composition may be a paste, putty, hydrogel, coated microsphere composition, and/or microsphere-encapsulated composition, such as described elsewhere herein. Such compositions can conveniently be placed into, for example, holes, gaps, or spaces of any shape or thickness in tissues and organs so as to substantially fill such holes, gaps, or spaces. In one embodiment, such holes, or gaps or spaces, are cartilage lesions in various full and partial thickness cartilage defects. In the present method of treating osteochondral defects, non-limiting embodiments and specific examples of the compositions used and the methods of making these compositions are described herein.

Before further describing various embodiments of the compositions and methods of the present disclosure in more detail by way of exemplary description, examples, and results, it is to be understood that the embodiments of the present disclosure are not limited in application to the details of methods and compositions as set forth in the following description. The embodiments of the compositions and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

Abbreviations which may be used herein include:
autologous chondrocyte implantation (ACI)
extracellular matrix (ECM)
mesenchymal stem cells (MSCs)
rat bone marrow mesenchymal stem cells (rBMSCs)
Tissue Culture Treated (TCT)
hyaluronic acid (HA)
pentanoate-functionalized hyaluronic acid (PHA)
real-time polymerase chain reaction (rt-PCR)
nuclear magnetic resonance NMR
hyaluronic acid-gelatin (H A-gelatin)
poly(L-lactic acid) (PLLA)
poly(lactic acid) (PLA)
poly(lactic-co-glycolic) acid (PLGA)
hydroxypropyl cellulose (HPC)
poly(2-hydroxyethylmethacrylate (PHEMA)
poly(ethylene glycol)-dimethacrylate (PEGDMA)
poly(ethylene glycol) diacrylate (PEGDA)
methacrylated gelatin (GelMA)
poly(ethylene oxide) (PEO)
polyethylene glycol-polylactic acid (PEG-PLA)
polyethylene glycol-polylactic acid-poly vinyl alcohol (PEG-PLA-PVA)
polyethylene glycol-poly(lactic-co-glycolic)-poly vinyl alcohol (PEG-PLGA-PEG)
polycaprolactone-PEG (PEG-PCL)
polylactic acid-polyethylene glycol-polylactic acid (PLA-PEG-PLA)
poly(3-hydroxybutyrate) (PHB)
poly(propylene fumarate-co-ethylene glycol) (P(PF-co-EG))
poly(polyethylene glycol-poly(butylene oxide) terephthalate) (P(PEG/PBO terephthalate))
polyethylene glycol-bis-polylactic acid-acrylate (PEG-bis-PLA-acrylate)
polyethylene glycol-g-poly(acrylamide-co-vinyl amine) (PEG-g-P(Aam-co-Vamine))
poly(acrylamide) (PAAm)
N-isopropylacrylamide (NIPA)
poly(N-isopropyl acrylamide-co-acrylic acid) (P(NIPAAm-co-Aac)
poly(N-isopropyl acrylamide-co-ethymethacrylate) P(NIPAAm-co-EMA)
poly(vinyl alcohol) (PVA)
poly(vinylpyrrolidone) (PVP)
ethylenevinylalcohol (EVAL)
poly(vinyl acrylic acid/vinyl alcohol) PVAc/PVA
poly(N-vinylpyrrolidone) PNVP
poly(methyl methacrylate-co-hydroxyethyl methacrylate) P(MMA-co-HEMA)
poly(acrylonitrile-co-allyl sulfonate) P(AN-co-allyl sulfonate), and
poly(glucosylthyl methacrylate-sulfate) P(GEMA-sulfate).

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein, including U.S. Published Patent Applications 20160038643 and 20170065742, and U.S. Pat. No. 8,715,983.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CAB ABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, percentage, temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, as well as 1.1, 1.2, 1.3, 1.4, 1.5, etc., 2.1, 2.2, 2.3, 2.4, 2.5, etc., and so forth, where the range is not limited solely to integers. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability of an active agent to modify the physiological system of an organism without reference to how the active agent has its physiological effects.

As used herein, "pure," "substantially pure," or "isolated" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The terms "subject" and "patient" are used interchangeably herein and will be understood to refer an organism to which the compositions of the present disclosure are applied and used, such as a vertebrate or more particularly to a warm blooded animal, such as a mammal. Non-limiting examples of animals within the scope and meaning of this term include dogs, cats, rats, mice, guinea pigs, chinchillas, horses, goats, cattle, sheep, llamas, zoo animals, Old and New World monkeys, non-human primates, and humans.

"Treatment" refers to therapeutic treatments, such as for healing or restoration of damaged cartilage. The term "treating" refers to administering the composition to a patient such therapeutic purposes, and may result in an amelioration of the condition or disease. Examples of such conditions which may be treated by the disclosed compositions include but are not limited to osteoarthritis, trauma arthritis, autoimmune arthritis, and joint injuries due to trauma, tearing or overuse.

The terms "therapeutic composition" and "pharmaceutical composition" refer to an active agent composition, such as the hydrogel compositions described herein, that may be administered to a subject by any method known in the art or otherwise contemplated herein, wherein administration of the composition brings about a therapeutic effect as described elsewhere herein. In addition, certain compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as toxicity, irritation and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by a person of ordinary skill in the art using routine experimentation based on the information provided herein.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Specific amino acids (i.e., the "natural amino acids") may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V.

The term "chondroinductive" as used herein refers to a material able to induce, guide, facilitate, or cause differentiation of any stem cell toward a chondrogenic lineage, i.e., to lead to cell morphology, markers, and/or behavior consistent with chondrocytes.

The term "hyaluronic acid" or "HA" refers to polymers of repeating disaccharide units composed of D-glucuronic acid and N-acetyl-D-glucosamine, and is also intended to refer to salts of hyaluronic acid. In a non-limiting embodiment, the HA is functionalized with pentanoate groups to for pentanoate-functionalized hyaluronic acid (PHA). Any other method of functionalization which enables the HA to function in accordance with the present disclosure may be used.

The term "crosslinked" as used herein refers, in at least one embodiment, to an HA molecule (or other crosslinkable polymer) with at least one covalent bond that is not found within the repeating disaccharide units of the HA or found between repeating units of the HA molecule, for example, it may refer to covalent linkage of two or more HA molecules via thiolated tissue particles or to intramolecular covalent linkage via thiolated tissue particles. In at least certain embodiments the average molecular weight of the HA (or salts thereof) used in the hydrogels of the present disclosure is within a range of 1 kDA to 20,000 kDa, or more particularly within a range of 3 kDa to 5,000 kDa, and more particularly within a range of about 10 kDa to about 2,000 kDa.

The term "hydrogel", as used herein, refers to a water-soluble cross-linked network of polymer chains. Hydrogels may be prepared from natural polymers (functionalized or non-functionalized) that include, but are not limited to, collagen, HA, HA-gelatin, chitosan, gelatin, alginate, pectin, carrageenan, chondroitin sulfate, dextran sulfate, polylysine, carboxymethyl chitin, fibrin, dextran, agarose, and pullulan. Hydrogels also may be prepared from synthetic polymers that include, but are not limited to, PLLA. PLA, PLGA, PHEMA, PEGDMA, PEGDA, GelMA, polyphazene, PEO and its copolymers, polyesters such as PEG-PLA, PEG-PLA-PVA, PEG-PLGA-PEG, PEG-PCL, PLA-PEG-PLA, PHB, P(PF-co-EG) plus or minus acrylate end groups, P(PEG/PBO terephthalate), PEG-bis-PLA-acrylate, PEG-g-P(Aam-co-Vamine), PAAm, P(NIPAAm-co-Aac, P(NIPAAm-co-EMA), PVA, PVAc/PVA, PNVP, P(MMA-co-HEMA), P(AN-co-allyl sulfonate), P(biscarboxy-phenoxy-phosphazine), and P(GEMA-sulfate).

Hydrogels may be prepared from both natural and synthetic polymers, examples of which include, but are not limited to, P(PEG-co-peptides), alginate-g-poly(ethylene oxide)-poly(propylene oxide)-poly(ethylene oxide) (alginate-g-(PEO—PPO—PEO), poly(poly(lactic-co-glycolic) acid-co-serine (P(PLGA-co-serine)), collagen-acrylate, alginate-acrylate, poly(hydroxypropyl methacrylate)-g-peptide (P(HPMA-g-peptide)), poly(hydroxyethyl methacrylate/Matrigel) (P(hema/Matrigel)), and hyaluronic acid-g-N-isopropyl acrylamide (HA-g-NIPAAm). In some embodiments, the hydrogel comprises a polymerized polyalkyleneglycolyl diacrylate. In another embodiment, the hydrogel comprises polyalkyleneglycolyl monoacrylates, including methacrylates. In yet another embodiment, the hydrogel comprises hyaluronic acid, chitosan, agarose, polyvinylacetate, polyvinylpyrrolide, or polyvinylalcohol nanoparticles.

In one non-limiting embodiment, the term "hydrogel" refers to a three-dimensional crosslinked network comprising hyaluronic acid, and optionally tissue particles, that contains a large amount amount of water, generally 50 wt % or more. A "hydrogel precursor" is a composition comprising hyaluronic acid, and optionally tissue particles, that contains a large amount amount of water and is capable of becoming crosslinked to form a hydrogel.

Where used herein, the term "heterologous" refers to a peptide or gene sequence which is not normally present in a given host proteome or genome in the same context in which the presently disclosed chondroinductive sequence is found. The heterologous sequence may be artificial or synthetic. Thus, where a heterologous linker sequence is natural, it is not naturally found adjacent to the chondroinductive peptide sequence, and thus its combination with the chondroinductive peptide sequence is an artificial construct. Where a heterologous linker sequence is artificial, it is similarly not naturally found adjacent to the chondroinductive peptide sequence, and thus its combination with the chondroinductive peptide sequence is an artificial construct. In one example, although the SPPEPS (SEQ ID NO: 2) peptide is a subsequence of aggrecan protein, the linker peptide attached to the SPPEPS (SEQ ID NO: 2) sequence herein is not a sequence which occur adjacent to SPPEPS (SEQ ID NO:2) in a natural protein, thus the linker-SPPEPS (SEQ ID NO:2) sequence is artificial.

Where used herein, the term "RGD" peptide refers to a peptide having the at least three amino acid residue motif "arginine-glycine-aspartic acid", and having cell adhesion properties. Examples of such RGD peptides include, but are not limited to, peptides having the amino acid sequences RGD, RGDS (SEQ ID NO: 67), RGDSP (SEQ ID NO:3), GCGYGRGDSP (SEQ ID NO:6), GRGDS (SEQ ID NO: 10), GRGDNP (SEQ ID NO:11), GRGDTP (SEQ ID NO:12), GRGDSPK (SEQ ID NO:13), RGDSPASSKP (SEQ ID NO: 14), and CGGNGEPRGDTYRAY (SEQ ID NO:15).

Returning to discussion of particular embodiments of the present disclosure, in at least certain embodiments the biomaterials are non-cellular. A synthetic, non-cellular material holds several clinical and business advantages over cell-based therapies, where associated challenges include harvesting sufficient cell numbers, the need for two separate procedures (harvest and implantation), inherent cost, logistical challenges, GMP requirements, insurance reimbursement, regulatory challenges, and required surgical training. Compared to a cell-based strategy, simple placement of a chondroinductive biomaterial such as disclosed herein, is easier for a surgeon to accomplish. Moreover, this approach takes advantage of synthetic materials, which compared to natural biomaterials are reproducible in large amounts with low cost, removing the animal-derived components eliminates any risk involved with immunogenesis and therefore leads into designing a biomaterial with a more straightforward regulatory pathway. The cost savings (from eliminating both cells and natural material), the single arthroscopic surgery, reproducibility and zero risk involved with material immunogenesis create a better business model ad have the potential to revolutionize orthopedic surgery. Significance and impact of the presently disclosed synthetic chondroinductive materials include, for example, (1) decreased recovery time and hyaline-like cartilage regeneration, (2) reproducibility in large amounts with lower cost, and (3) low risk of immunogenesis.

In alternate embodiments, the chondroinductive peptides of the present disclosure may comprise an amino acid sequence -$X_1$-$X_2$-$X_3$-$X_4$-$X_5$-$X_6$-(SEQ ID NO:1), wherein $X_1$ and $X_6$ are independently selected from serine and threonine; $X_2$, $X_3$ and $X_5$ are independently selected from proline, 3-hydroxyproline, and 4-hydroxyproline; and $X_4$ is glutamic acid or aspartic acid. As noted above, in at least one embodiment, $X_1$ is ser, $X_2$ is pro, $X_3$ is pro, $X_4$ is glu, $X_5$ is pro, and $X_6$ is ser (SPPEPS—SEQ ID NO:2). In at least certain embodiments, the chondroinductive peptide may comprise from 6 to about 50 amino acids, including from 1 up to about 44 additional amino acids (e.g., a linker sequence) extending from the N-terminal and/or C-terminal end of the core peptide (i.e., SEQ ID NO:1 or 2). The chondroinductive and/or cell adhesion peptides of the present disclosure optionally may be linked to heterologous peptide linker sequences which serve to link the chondroinductive peptide and/or cell adhesion peptide to the functionalized HA molecules. In one embodiment, the heterologous linker sequence is GCGYG (SEQ ID NO:4). However, any other heterologous linker sequence which enables the chondroinductive peptide and/or cell adhesion peptide to retain its activity when linked to the HA molecule is considered to be suitable for use in the compositions of the present disclosure. Non-limiting examples of peptide linker sequences which may be used in the peptide sequences of the present disclosure include, but are not limited to, those shown in U.S. Pat. Nos. 9,409,950, 9,827,272, and 9,937,256. In certain embodiments the linker peptide comprises a cysteine residue. The linker peptide may be constructed to include from 1 to 25, or more, amino acid residues selected from the 20 "natural amino acids" (or any other amino acid that enables the linker to function in accordance with the present embodiments.

The composition may comprise cell adhesion peptides other than RGD-motif peptides, such as but not limited to, the peptides having the amino acid sequences SEQ ID NOS:16-21 or others (see Table 1). A non-inclusive list of cell adhesion peptides that can be used in various embodiments of the present disclosure is shown in Table 1.

TABLE 1

Cell Adhesion peptides

| Source Protein | Amino Acid Sequence | SEQ ID NO: |
|---|---|---|
|  | RGD |  |
|  | RGDS | 67 |
|  | RGDSP | 3 |
|  | GCGYGRGDSP | 6 |
| FN | GRGDS | 10 |
|  | GRGDNP | 11 |
|  | GRGDTP | 12 |
|  | GRGDSPK | 13 |
|  | RGDSPASSKP | 14 |
| OPN | CGGNGEPRGDTYRAY | 15 |
|  | CGGNRWHSIYITRFG | 16 |
|  | CGGEILDVPST | 17 |
|  | CGGRKRLQVQLSIRT | 18 |
|  | CGGKAFDITYVRLKF | 19 |
|  | RNIAEIIKDIGC | 20 |
|  | CGGVSWFSRHRYSPFAVS | 21 |
| COL I | GFOGER | 22 |
|  | DGEA | 23 |
| LAM | YIGSR | 24 |
|  | YIGSR (cyclic) | 25 |
|  | SIKVAV | 26 |
|  | IKVAV | 27 |
|  | IKLLI | 28 |
|  | LRGDN | 29 |
|  | SINNNR | 30 |
| LAMg1 | LRE |  |
|  | PDGSR | 31 |
|  | GTFALRGDNGQ | 32 |
|  | CFALRGDNP | 33 |
|  | NPWHSIYITRFG | 34 |
|  | TWYKIAFQRNRK | 35 |
|  | KAFDITYVRLKF | 36 |
|  | LGTIPG | 37 |

TABLE 1-continued

Cell Adhesion peptides

| Source Protein | Amino Acid Sequence | SEQ ID NO: |
|---|---|---|
| FN | PKRGDL | 38 |
|  | NGRAHA | 39 |
|  | GACRGDCLGA (cyclic) | 40 |
|  | IDAPS | 41 |
|  | REDV | 42 |
|  | PHSRN | 43 |
|  | KQAGDV | 44 |
|  | LDV |  |
|  | WQPPRARI | 45 |
|  | SPPRRARV | 46 |
|  | LIGRKK | 47 |
|  | IWKHKGRDVILKKDVRFYC | 48 |
|  | KLDAPT (FN5) | 49 |
|  | PRARI (FN12-14) | 50 |
| VTN | CKKQRFRHRNRKG | 51 |
| OPN | KRSR | 52 |
|  | FHRRIKA | 53 |
|  | SVVYGLR | 54 |
|  | ELVTDFPTDLPAT | 55 |
| ELN | VPGIG | 56 |
|  | VGVAPG | 57 |
| COL IV | CNYYSNS | 58 |
|  | MNYYSNS | 59 |
| THBS1 | CSVTCG | 60 |
|  | GRGDAC | 61 |
|  | FQGVLQNVRFVF | 62 |
|  | AELDVP | 63 |
|  | VALDEP | 64 |
| NID 1 | GFRGDGQ | 65 |
|  | SIGFRGDGQTC | 66 |

Table 1 Abbreviations: COL I, collagen I; COL IV, collagen IV; ELN, elastin; FC, formal charge at pH 7; FN1, fibronectin; IEP, isoelectric point; LAM, laminin; LAMg1, laminin g1; NID 1, nidogen-1, closed at the * interface; OPN, osteopontin; THBS1, thrombospondin; VTN, vitronectin.

In certain embodiments, the scaffold with which the chondroinductive peptide is associated is made up of polymer microspheres. In one embodiment, the microsphere-based scaffolds can be prepared from PHA or PLGA microspheres. However, the microspheres can be prepared from substantially any polymer, such as biocompatible, bioerodable, and/or biodegradable polymers. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, poly anhydrides, polyanhydride-co-imides, polyesters, polyorthoesters, polycaprolactones, polyesters, poly anhydrides, polyphosphazenes, poly(phosphoesters), polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, EVAL copolymers, propylenevinyl-alcohol copolymers, PVP, poly(L-lysine), poly(lactic acid-co-lysine), poly(lactic acid-graft-lysine), polyanhydrides (such as poly(fatty acid dimer), poly(fumaric acid), poly (sebacic acid), poly(carboxyphenoxy propane), poly(carboxyphenoxy hexane), poly(anhydride-co-imides), poly (amides), poly(iminocarbonates), poly(urethanes), poly (organophasphazenes), poly(phosphates), poly(ethylene vinyl acetate) and other acyl substituted cellulose acetates and derivatives thereof, poly(amino acids), poly(acrylates), polyacetals, poly(cyanoacrylates), poly(styrenes), poly(vinyl chloride), poly(vinyl fluoride), polyvinyl imidazole), chlorosulfonated polyolefins, polyethylene oxide, combinations thereof, polymers having monomers thereof, or the like. In certain aspects, the nanoparticles include HPC, NIPA, polyethylene glycol, PVA, polyethylenimine, chitosan, chitin, dextran sulfate, heparin, chondroitin sulfate, gelatin, etc. and their derivatives, co-polymers, and mixtures thereof. A non-limiting method for making nanoparticles is described in U.S. Publication 2003/0138490, the entirety of which is incorporated by reference.

In one embodiment, the present disclosure is directed to a tissue engineering scaffold comprising polymer microspheres in contact with the chondroinductive peptide, wherein the peptide is intimately mixed with the microsphere polymers, is a coating on the microsphere polymers, and/or is encapsulated in said microspheres that assemble the scaffold. Therefore, the present invention also provides a tissue engineering scaffold comprising particles comprising microspheres mixed with, coated with, and/or encapsulating a chondroinductive peptide.

In one embodiment, the present disclosure provides a method for coating microspheres with the chondroinductive peptide generally comprising the steps of: (a) providing a solution or suspension of one or more types of the chondroinductive peptide; (b) suspending microspheres in solution for lyophilization; (c) assembling scaffolds by flowing lyophilized microsphere suspension into a three dimensional mold; (d) contacting the scaffolds with the chondroinductive peptide solution for a time sufficient for the chondroinductive peptide to attach to the microspheres forming the scaffolds; and (e) removing the scaffolds for lyophilization. The method may further comprise a step of fabricating microspheres before step (b). The methods of making the scaffolds from the microspheres may include the use of a solvent or solvent system (i.e., media or media system) that is compatible with the particular polymer of the microsphere, which polymers have been described above and incorporated herein. The solvent or solvent system selected to mold the microspheres together are described herein. Examples of some solvents can include hexane, benzene, toluene, diethyl ether, chloroform, ethyl acetate, 1,4-dioxane, tetrahydrofuran, dichloromethane, acetone, acetonitrile, dimethylformamide, dimethyl sulfoxide, acetic acid, n-butanol, 2-butanol, 3-butanol, t-butyl alcohol, carbon tetrachloride, chlorobenzene, isopropanol, n-propanol, ethanol, methanol, formic acid, water, cyclohexane, 1,2-dichloroethane, diethyl ether, diethylene glycol, diglyme, dimethyl ether, dioxane, ethylene glycol, glycerin, heptane, hexamethylphosphoramide, hesamethylphosphorous triamide, hexane, nitromethane, pentane, petroleum ether, propanol, pyridine, o-xylene, m-xylene, p-xylene, and the like. Carbon dioxide can also be used as a solvent or media to meld the microspheres together. Additionally, solvents known to be useful with particular polymers can be used or combined with the solvents described herein.

In another embodiment, the present disclosure provides a method for encapsulating the chondroinductive peptide in a microsphere polymer, which comprises the steps of: (a) providing a solution or suspension of one or more types of the chondroinductive peptide; (b) providing an encapsulating solution containing the chondroinductive peptide solution and microsphere polymer, wherein the microsphere polymer is insoluble in the encapsulating solution, and (c) fabricating microspheres encapsulating the chondroinductive peptide. The method of fabricating microspheres is described elsewhere herein. In one embodiment, the encapsulating solution step (b) comprises between about 0.01 w/v % and about 90 w/v % chondroinductive peptide and between about 10 w/v % and about 90 w/v % microsphere polymer. Suitable microsphere polymers have been described elsewhere herein. In one non-limiting embodiment, the microsphere polymer is PLGA.

The scaffolds described herein may further comprise one or more therapeutic agents that are useful in applications of the chondroinductive scaffolds. Exemplary therapeutic agents include, but are not limited to: anti-proliferative/antimitotic agents including natural products such as vinca alkaloids (i.e., vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II$_b$/HI a inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e., estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives e.g., aspirin; para-aminophenol derivatives, e.g., acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligonucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors; beta$_2$ agonists (e.g., salbutamol, terbutaline, clenbuterol, salmeterol, formoterol); steroids such glycocorticosteroids, preferably anti-inflammatory drugs (e.g., Ciclesonide, Mometasone, Flunisolide, Triamcinolone, Beclomethasone, Budesonide, Fluticasone); anticholinergic drugs (e.g., ipratropium, tiotropium, oxitropium); leukotriene antagonists (e.g., zafirlukast, montelukast, pranlukast); xantines (e.g., aminophylline, theobromine, theophylline); Mast cell stabilizers (e.g., cromoglicate, nedocromil); inhibitors of leukotriene synthesis (e.g., azelastina, oxatomide ketotifen); mucolytics (e.g., N-acetylcysteine, carbocysteine); antibiotics, (e.g., Aminoglycosides such as, amikacin, gentamicin, kanamycin, neomycin, netilmicin streptomycin, tobramycin; Carbacephem such as loracarbef, Carbapenems such as ertapenem, imipenem/cilastatin meropenem; Cephalosporins—first generation—such as cefadroxil, cefaxolin, cephalexin; Cephalosporins—second generation—such as cefaclor, cefamandole, defoxitin, cefproxil, cefuroxime; Cephalosporins—third generation—cefixime, cefdinir, ceftaxidime, defotaxime, cefpodoxime, ceftriaxone; Cephalosporins—fourth generation—such as maxipime; Glycopeptides such as vancomycin, teicoplanin; Macrolides such as azithromycin, clarithromycin, Dirithromycin, Erythromycin, troleandomycin; Monobactam such as aztreonam; Penicillins such as Amoxicillin, Ampicillin, Azlocillin, Carbenicillin, Cloxacillin, Dicloxacillin, Flucloxacillin, Mezlocillin, Nafcillin, Penicillin, Piperacillin, Ticarcillin; Polypeptides such as bacitracin, colistin, polymyxin B; Quinolones such as Ciprofloxacin, Enoxacin, Gatifloxacin, Levofloxacin, Lomefloxacin, Moxifloxacin, Norfloxacin, Ofloxacin, Trovafloxacin; Sulfonamides such as Mafenide, Prontosil, Sulfacetamide, Sulfamethizole, Sulfanamide, Sulfasalazine, Sulfisoxazole, Trimethoprim, Trimethoprim-Sulfamethoxazole Co-trimoxazole (TMP-SMX); Tetracyclines such as Demeclocycline, Doxycycline, Minocycline, Oxytetracycline, Tetracycline; Others such as Chloramphenicol, Clindamycin, Ethambutol, Fosfomycin, Furazolidone, Isoniazid, Linezolid, Metronidazole, Nitrofurantoin, Pyrazinamide, Quinupristin/Dalfopristin, Rifampin, Spectinomycin); pain relievers in general such as analgesic and antiinflammatory drugs, including steroids (e.g., hydrocortisone, cortisone acetate, prednisone, prednisolone, methylprednisolone, dexamethasone, betamethasone, triamcinolone, beclometasone, fludrocortisone acetate, deoxycorticosterone acetate, aldosterone); and non-steroid antiinflammatory drugs (e.g., Salicylates such as aspirin, amoxiprin, benorilate, coline magnesium salicylate, diflunisal, faislamine, methyl salicylate, salicyl salicylate); Arylalkanoic acids such as diclofenac, aceclofenac, acematicin, etodolac, indometacin, ketorolac, nabumetone, sulindac tolmetin; 2-Arylpropionic acids (profens) such as ibuprofen, carprofen, fenbufen, fenoprofen, flurbiprofen, ketoprofen, loxoprofen, naproxen, tiaprofenic acid; N-arylanthranilic acids (fenamic acids) such as mefenamic acid, meclofenamic acid, tolfenamic acid; Pyrazolidine derivatives such as phenylbutazone, azapropazone, metamizole, oxyphenbutazone; Oxicams such as piroxicam, meloxicam, tenoxicam; Coxib such as celecoxib, etoricoxib, lumiracoxib, parecoxib, rofecoxib (withdrawn from market), valdecoxib (withdrawn from market); Sulphonanilides such as nimesulide; others such as licofelone, omega-3 fatty acids; cardiovascular drugs such as glycosides (e.g., strophantin, digoxin, digitoxin, proscillaridine A); respiratory drugs; antiasthma agents; bronchodilators (adrenergics: albuterol, bitolterol, epinephrine, fenoterol, formoterol, isoetharine, isoproterenol, metaproterenol, pirbuterol, procaterol, salmeterol, terbutaline); anticancer agents (e.g., cyclophosphamide, doxorubicine, vincristine, methotrexate); alkaloids (i.e., ergot alkaloids) or triptans suchas sumatriptan, rizatriptan, naratriptan, zolmitriptan, eletriptan and almotriptan, than can be used against migraine; drugs (i.e., sulfonylurea) used against diabetes and related dysfunctions (e.g., metformin, chlorpropamide, glibenclamide, glicliazide, glimepiride, tolazamide, acarbose, pioglitazone, nateglinide, sitagliptin); sedative and hypnotic drugs (e.g., Barbiturates such as secobarbital, pentobarbital, amobarbital; uncategorized sedatives such as eszopiclone, ramelteon, methaqualone, ethchlorvynol, chloral hydrate, meprobamate, glutethimide, methyprylon); psychic energizers; appetite inhibitors (e.g., amphetamine); antiarthritis drugs (e.g., NSAIDs); antimalaria drugs (e.g., quinine, quinidine, mefloquine, halofantrine, primaquine, cloroquine, amodiaquine); antiepileptic drugs and anticonvulsant drugs such as Barbiturates, (e.g., Barbexaclone, Metharbital, Methylphenobarbital, Phenobarbital, Primidone), Succinimides (e.g., Ethosuximide, Mesuximide, Phensuximide), Benzodiazepines, Carboxamides (e.g., Carbamazepine, Oxcarbazepine, Rufinamide) Fatty acid derivatives (e.g., Valpromide, Valnoctamide); Carboxilyc acids (e.g., Valproic acid, Tiagabine); Gaba analogs (e.g., Gabapentin, Pregabalin, Progabide, Vigabatrin); Topiramate, Ureas (e.g., Phenacemide, Pheneturide), Carbamates (e.g., emylcamate Felbamate, Meprobamate); Pyrrolidines (e.g., Levetiracetam Nefiracetam, Seletracetam); Sulfa drugs (e.g., Acetazolamide, Ethoxzolamide, Sultiame, Zonisamide) Beclamide; Paraldehyde, Potassium bromide; antithrombotic drugs such as Vitamin K antagonists (e.g., Acenocoumarol, Dicumarol, Phenprocoumon, Phenindione, Warfarin); Platelet aggregation inhibitors (e.g., antithrombin III, Bemiparin, Deltaparin, Danaparoid, Enoxaparin, Heparin, Nadroparin, Pamaparin, Reviparin, Tinzaparin); other platelet aggregation inhibitors (e.g., Abciximab, Acetylsalicylic acid, Aloxiprin, Ditazole, Clopidogrel, Dipyridamole, Epoprostenol, Eptifibatide, Indobufen, Prasugrel, Ticlopidine, Tirofiban, Treprostinil, Trifusal); Enzymes (e.g., Alteplase, Ancrod, Anistreplase, Fibrinolysin, Streptokinase, Tenecteplase, Urokinase); Direct thrombin inhibitors (e.g., Argatroban, Bivalirudin. Lepirudin, Melagatran, Ximelagratan); other antithrombotics (e.g., Dabigatran, Defibrotide, Dermatan sulfate, Fondaparinux, Rivaroxaban); antihypertensive drugs such as Diuretics (e.g., Bumetanide, Furosemide, Torsemide, Chlortalidone, Hy drocloro thiazide, Chlorothiazide, Indapamide, metolaxone, Amiloride, Triamterene); Antiadrenergics (e.g., atenolol, metoprolol, oxprenolol, pindolol, propranolol, doxazosin, prazosin, teraxosin, labetalol); Calcium channel blockers (e.g., Amlodipine, felodipine, dsradipine, nifedipine, nimodipine, diltiazem, verapamil); Ace inhibitors (e.g., captopril, enalapril, fosinopril, lisinopril, perindopril, quinapril, ramipril, benzapril); Angiotensin II receptor antagonists (e.g., candesartan, irbesartan, losartan, telmisartan, valsartan); Aldosterone antagonists such as spironolactone; centrally acting adrenergic drugs (e.g., clonidine, guanabenz, methyldopa); antiarrhythmic drug of Class I that interfere with the sodium channel (e.g., quinidine, procainamide, disodyramide, lidocaine, mexiletine, tocamide, phenyloin, encamide, flecamide, moricizine, propafenone), Class II that are beta blockers (e.g., esmolol, propranolol, metoprolol); Class III that affect potassium efflux (e.g., amiodarone, azimilide, bretylium, clorilium, dofetilide, tedisamil, ibutilide, sematilide, sotalol); Class IV that affect the AV node (e.g., verapamil, diltiazem); Class V unknown mechanisms (e.g., adenoide, digoxin); antioxidant drugs such as Vitamin A, vitamin C, vitamin E, Coenzime Q10, melanonin, carotenoid terpenoids, non-carotenoid terpenoids, flavonoid polyphenolic; antidepressants (e.g., mirtazapine, trazodone); antipsychotic drugs (e.g., fluphenazine, haloperidol, thiotixene, trifluoroperazine, loxapine, perphenazine, clozapine, quetiapine, risperidone, olanzapine); anxyolitics (Benzodiazepines such as diazepam, clonazepam, alprazolam, temazepam, chlordiazepoxide, flunitrazepam, lorazepam, clorazepam; Imidaxopyridines such as Zolpidem, alpidem; Pyrazolopyrimidines such as zaleplon); antiemetic drugs such as Serotonine receptor antagonists (dolasetron, granisetron, ondansetron), dopamine antagonists (domperidone, droperidol, haloperidol, chlorpromazine, promethazine, metoclopramide) antihystamines (cyclizine, diphenydramine, dimenhydrinate, meclizine, promethazine, hydroxyzine); antiinfectives; antihystamines (e.g., mepyramine, antazoline, diphenhydramine, carbinoxamine, doxylamine, clemastine, dimethydrinate, cyclizine, chlorcyclizine, hydroxyzine, meclizine, promethazine, cyproheptadine, azatidine, ketotifen, acrivastina, loratadine, terfenadine, cetrizidinem, azelastine, levocabastine, olopatadine, levocetrizine, desloratadine, fexofenadine, cromoglicate nedocromil, thiperamide, impromidine); antifungus (e.g., Nystatin, amphotericin B, natamycin, rimocidin, filipin, pimaricin, miconazole, ketoconazole, clotrimazole, econazole, mebendazole, bifonazole, oxiconazole, sertaconazole, sulconazole, tiaconazole, fluconazole, itraconazole, posaconazole, voriconazole, terbinafine, amorolfine, butenafine, anidulafungin, caspofungin, flucytosine, griseofulvin, fluocinonide) and antiviral drugs such as Anti-herpesvirus agents (e.g., Aciclovir, Cidofovir, Docosanol, Famciclovir, Fomivirsen, Foscarnet, Ganciclovir, Idoxuridine, Penciclovir, Trifluridine, Tromantadine, Valaciclovir, Valganciclovir, Vidarabine); Anti-influenza agents (Amantadine, Oseltamivir, Peramivir, Rimantadine, Zanamivir); Antiretroviral drugs (abacavir, didanosine, emtricitabine, lamivudine, stavudine, tenofovir, zalcitabine, zidovudine, adeforvir, tenofovir, efavirenz, delavirdine, nevirapine, amprenavir, atazanavir, darunavir, fosamprenavir, indinavir, lopinavir, nelfinavir, ritonavir, saquinavir, tipranavir); other antiviral agents (Enfuvirtide, Fomivirsen, Imiquimod, Inosine, Interferon, Podophyllotoxin, Ribavirin, Viramidine); drugs against neurological dysfunctions such as Parkinson's disease (e.g., dopamine agonists, L-dopa, Carbidopa, benzerazide, bromocriptine, pergolide, pramipexole, ropinipole, apomorphine, lisuride); drugs for the treatment of alcoholism (e.g., antabuse, naltrexone, vivitrol), and other addiction forms; vasodilators for the treatment of erectile dysfunction (e.g., Sildenafil, vardenafil, tadalafil), muscle relaxants (e.g., benzodiazepines, methocarbamol, baclofen, carisoprodol, chlorzoxazone, cyclobenzaprine, dantrolene, metaxalone, orphenadrine, tizanidine); muscle contractors; opioids; stimulating drugs (e.g., amphetamine, cocaine, caffeine, nicotine); tranquillizers; antibiotics such as macrolides; aminoglycosides; fluoroquinolones and beta-lactams; vaccines; cytokines; growth factors; hormones including birth-control drugs; sympathomimetic drugs (e.g., amphetamine, benzylpiperazine, cathinone, chlorphentermine, clobenzolex, cocaine, cyclopentamine, ephedrine, fenfluramine, methylone, methylphenidate, Pemoline, phendimetrazine, phentermine, phenylephrine, propylhexedrine, pseudoephedrine, sibutramine, symephrine); diuretics; lipid regulator agents; antiandrogen agents (e.g., bicalutamide, cyproterone, flutamide, nilutamide); antiparasitics; blood thinners (e.g., warfarin); neoplastic drugs; antineoplastic drugs (e.g., chlorambucil, chloromethine, cyclophosphamide, melphalan, carmustine, fotemustine, lomustine, carboplatin, busulfan, dacarbazine, procarbazine, thioTEPA, uramustine, mechloretamine, methotrexate, cladribine, clofarabine, fludarabine, mercaptopurine, fluorouracil, vinblastine, vincristine, daunorubicin, epirubicin, bleomycin, hydroxyurea, alemtuzumar, cetuximab, aminolevulinic acid, altretamine, amsacrine, anagrelide, pentostatin, tretinoin); hypoglicaemics; nutritive and integrator agents; growth integrators; antienteric drugs; vaccines; antibodies; diagnosis and radioopaque agents; or mixtures of the above mentioned drugs (e.g., combinations for the treatment of asthma containing steroids and beta-agonists); or any other biologically active agent such as nucleic acids, DNA, RNA, siRNA, polypeptides, antibodies, and the like. Growth factors and adhesion peptides can also be useful for tissue development within a subject and can be included in or with the scaffolds.

EXAMPLES

Certain embodiments of the present disclosure will now be discussed in terms of several specific, non-limiting, examples. The examples described below will serve to illustrate the general practice of the present disclosure, it being understood that the particulars shown are merely exemplary for purposes of illustrative discussion of particular embodiments of the present disclosure only and are not intended to be limiting of the claims of the present disclosure.

Example 1

Methods
Synthesis of Pentenoate-Functionalized Hyaluronic Acid (PHA)

PHA was synthesized as described in Townsend, 2018 (Townsend J. M., B. T. Andrews, Y. Feng, J. Wang, R. J. Nudo, E. Van Kampen, S. H. Gehrke, C. J. Berkland, and M. S. Detamore. Superior calvarial bone regeneration using pentenoate-functionalized hyaluronic acid hydrogels with devitalized tendon particles. *Acta Biomater.* 71:148-155, 2018). Briefly, Hyaluronic acid (HA, Mw=60 KDa, Lifecore Biomedical, Chaska, MN) was fully dissolved in DI water to 0.5% (w/v) before dropwise addition of dimethyifonnarnide (DMF) to reach a 3:2 ratio of water:DMF. Simultaneously, 5M pentenoic anhydride (Cat #471801, Sigma-Aldrich, St. Louis, MO) was slowly added to the solution in excess relative to HA. When adding the DMF and pentenoic anhydride was complete, the solution pH was maintained at 8-9 by slow dropwise addition of 1M NaOH during constant monitoring of the PH for 5 hours. The conjugation reaction was completed overnight to form PHA. The next day, solid NaCl was added to the solution to reach the final concentration of 0.5M NaCl. After the salt was fully dissolved, the polymer was precipitated by adding acetone (water/acetone (v/v) ratio of 1:4) and centrifuging the solution at 7,000×g for 5 minutes. After centrifuging, the PHA was completely precipitated in the form of pellets. The pellets were dissolved in DI water and dialyzed against DI water for 48 hours, exchanging the DI water every 12 hours. After dialysis, dry PHA was frozen, lyophilized, and stored at −20° C.

PHA Hydrogel Preparation, Peptide Conjugation, and Surface Analysis

To prepare PHA hydrogels (without peptide incorporation), a solution of phosphate-buffered saline (PBS) containing 2.3 mM 2-Hydroxy-4'-(2-hydroxyethoxy)-2-methylpropiophenone (Irgacure 2959, Cat #410896, Sigma-Aldrich) and 1% dithiothreitol (DTT, Cat #D0632, Sigma-Aldrich) was prepared and sterile-filtered (0.22 µm). The PHA was removed from the freezer and brought to room temperature and then sterilized using ethylene oxide gas (AN74i, Anderson Anprolene, Haw River, NC) and mixed with the PBS solution to reach 5% PHA concentration. The solution was left at room temperature for 2 hours to fully dissolve the PHA particles. 100 µL of this precursor solution was added to each well of a 48 well plate and briefly centrifuged before hydrogel crosslinking with a handheld 312 nm UV-light at 9 mW/cm² for 2 minutes (EB-160C, Spectroline, Westbury, NY).

To prepare PHA hydrogels with conjugated peptides, hydrogels were made in two steps. First, PHA was mixed with PBS solution containing 1 mM Irgacure and 1.5 mM thiolated peptide (e.g., see Table 2) to achieve a 2% (w/v) PHA solution. The solution was crosslinked with UV light for 2 minutes, and the crosslinking of the peptide to the PHA network was confirmed with H1NMR (Varian Mercury VNMRS 400 MHz spectrometer). This solution was then mixed with more PHA (to achieve final concentration of 5% (w/v)) and was mixed with PBS solution containing Irgacure and DTT to achieve 2 mM Irgacure concentration and 1% DTT. The solution was again crosslinked for 2 minutes to create the final hydrogels.

Cell Culture and SPPEPS (SEQ ID NO:2) Peptide Incorporation

Rat bone marrow MSCs from the tibias and femurs of 8 week-old male Sprague-Dawley Rats (ScienCell, Carlsbad, CA) were thawed and cultured to passage 4 in cell culture medium (minimum essential medium-alpha (Cat #12561072, Thermo Fisher Scientific, Waltham, MA) supplemented with 10% fetal bovine serum (FBS, Cat #16000044, Thermo Fisher Scientific) and 1% penicillin/streptomycin (Cat #15140-122, Thermo Fisher Scientific)). The cells were used immediately after passage 4. Peptides for conjugation to the PHA (see Table 2) were custom-ordered from Biosynthetic (Lewisville, TX) and were synthesized by PTI Symphony peptide synthesizer (Tucson, AZ) using solid-phase synthesis with Fluorenylmethyloxy-carbonyl protecting group (Fmoc) chemistry (i.e., Fmoc was used for the temporary protection of the N-terminus, and then cleaved from the resin using standard methods). Peptide identities were confirmed by Biosynthetic using mass spectroscopy, and purity was shown to be >95% using analytical high-performance liquid chromatography (HPLC, Shimadzu, Columbia, MD).

TABLE 2

List of synthesized peptides

| Peptide designation | Amino Acid Sequence | SEQ ID NO: | Description |
|---|---|---|---|
| | SPPEPS | 2 | chondroinductive peptide |
| | RGDSP | 3 | cell adhesion peptide |
| | GCGYG | 4 | linker sequence |
| | PSEPSP | 5 | scrambled SPPEPS (sham peptide) |
| RGD | GCGYGRGDSP | 6 | linker+RGDSP |
| SP | GCGYGSPPEPS | 7 | linker+SPPEPS |

TABLE 2-continued

List of synthesized peptides

| Peptide designation | Amino Acid Sequence | SEQ ID NO: | Description |
|---|---|---|---|
| PS | GCGYGPSEPSP | 8 | linker+PSEPSP |
| | DHLSDNYTLDHDRAIH | 9 | Link N sequence |

In one set of experimental groups, the SPPEPS (SEQ ID NO:2) peptide was adsorbed to the well plate surface. The peptide was dissolved in sterile DI water (20 µg/mL), sterile-filtered (0.22 µm), and was added to sterile 96-well plates to reach the desired coating concentrations (0.5, 1 and 3 µg/mm2) before overnight water evaporation at room temperature in sterile conditions. The rBMSCs were thawed and after passage 4 were cultured on the plates (150,000 cells/well, i.e., 23.5×106 cells/cm2), for the control groups the rBMSCs were cultured (150,000 cells/well) on the uncoated TCT plates and the cell culture medium was changed every second day.

In a separate set of experimental groups, SPPEPS (SEQ ID NO:2) peptide was included in soluble form in the medium instead of being coated on the surface. rBMSCs were cultured on 96-well plates (150,000 cells/well) with cell culture medium containing SPPEPS (SEQ ID NO:2) (50, 100 and 500 ng/ml). The cell culture medium containing the peptide was changed every second day.

Description of Experimental Design

In a preliminary study, the chondroinductivities of Link N peptide (SEQ ID NO: 9, Table 2) and SPPEPS (SEQ ID NO:2) with rBMSCs were evaluated at two plate coating densities (0.5 and 1 µg/mm2) and two soluble concentrations (10 and 100 ng/mL) after 3 days by rt-PCR (n=3). For rBMSCs cultured on TCT plates the chondroinductivity was compared with negative control (no growth factor or peptide in the cell culture medium) and positive control group. The positive control was a known chondrogenic growth factor in lieu of the SPPEPS (SEQ ID NO:2) peptide, i.e., 10 ng/ml (dissolved in rBMSCs cell culture medium) human transforming growth factor-β3 (TGF-β3, R&D systems, Minneapolis, MN).

rBMSCs were cultured either on TCT plastic plates or on a hydrogel-coated surface. For the cells cultured on TCT plates, three different concentrations of SPPEPS (SEQ ID NO:2) peptide (50, 100 and 500 ng/ml) in cell culture medium, three different coating concentrations (0.5, 1 and 3 µg/mm2) and a control group (no growth factor or peptide in the cell culture medium) were chosen (n=6) and the peptide chondroinductivity was evaluated by rt-PCR after 3 days (see FIGS. 2-4 and gene expression subsection below).

For the analysis of the rBMSCs cultured on the hydrogel-coated surfaces (results shown, for example, in FIGS. 1 and 5-7), a new group of rBMSCs from the same source was purchased and prepared until passage 4 using the cell culture methods described previously then were cultured on top of the hydrogels (30,000 cells/well, i.e., 47×10$^6$ cells/cm$^2$) and the medium (minimum essential medium-supplemented with 10% FBS and 1% penicillin/streptomycin) was changed every second day for 3 days (n=4). The rBMSCs on tissue culture plates served as the baseline control group and the chondroinductivities of PHA hydrogels were analyzed by rt-PCR after 3 days for various peptides which were conjugated to the PHA hydrogel (n=4).

Treatments were:
(1) TCT plate (a control);
(2) PHA=5% (w/v) pentanoate-functionalized hyaluronic acid with no peptide conjugation (a control);
(3) PHA+RGD=PHA conjugated to 1.5 mM GCGYGRGDSP (RGDSP conjugated to PHA via GCGYG linker);
(4) PHA+SP=PHA conjugated to 1.5 mM GCGYGSP-PEPS (SPPEPS conjugated to PHA via GCGYG linker);
(5) PHA+PS=PHA conjugated to 1.5 mM GCGYGPSEPSP (PSEPSP conjugated to PHA via GCGYG linker); and
(6) PHA+RGD+SP=PHA conjugated to 1.5 mM GCGYGRGDSP and 1.5 mM GCGYGSPPEPS.

The DNA contents of all the samples (TCT, PHA, PHA+RGD, PHA+SP, PHA+PS and PHA+RGD+SP) were measured after 3 days (n=4). The samples were digested overnight at 65° C. in 200 µL papain mixture (125 mg/mL papain from papaya latex, 5 mM N-acetyl cysteine, 5 mM EDTA, and 100 mM PBS) and the DNA content of the samples was measured using a PicoGreen assay kit (Thermo-Fisher Scientific, Waltham, MA, P7589) according to the manufacturer's instructions. All the samples were evaluated in triplicate.

Gene Expression

The gene expressions were analyzed for all the rBMSCs samples cultured on the TCT plates after 3 days (n=6) and all the rBMSCs cultured on the hydrogel surface after 3 days (n=4). The gene expressions of each sample were evaluated in triplicate. To prepare the samples for gene expression, the mRNAs were extracted after 3 days using Qiagen RNeasy mini kit (Valencia, CA) following the kit instructions, before reverse transcription using a cDNA kit (Invitrogen, Carlsbad, CA). rt-PCR was performed with a qTOWER$^3$ Thermal Cycler (Upland. CA) using TaqMan Col2A1, Sox9, ACAN and GAPDH primers (Invitrogen, Carlsbad, CA). GAPDH was used as an endogenous control, with relative gene expression measured using the $2^{-\Delta\Delta Ct}$ method. For cells on both surfaces, the calibrators were the rBMSCs at passage 4 before transferring them to the 96-well plates.

Statistical Analyses

For the statistical analyses, Tukey's HSD method was used for inter-group comparisons, and Dunnett's test was employed to compare the groups with the negative control. Calculations were performed with GraphPad Prism (Graphpad Software Inc., La Jolla, CA), with $p<0.05$ considered significant. The results for rt-PCR and PicoGreen were reported as the mean±standard deviation, with proteomics results reported as median±standard deviation.

Results

DNA Content

In the hydrogel surface analysis (FIG. 1), the DNA contents were in the range of 0.8 to 1.1 µg, with 34% and 27% higher DNA contents in the PHA and PHA+SP+RGD groups compared to the control (rBMSCs on TCT plates), respectively ($p<0.05$). In addition, comparing the DNA contents of hydrogel groups indicated that the DNA content of the PHA group was 36% and 32% higher compared to the PHA+RGD and PHA+SP groups respectively ($p<0.05$).

Gene Expression

Figure 2:
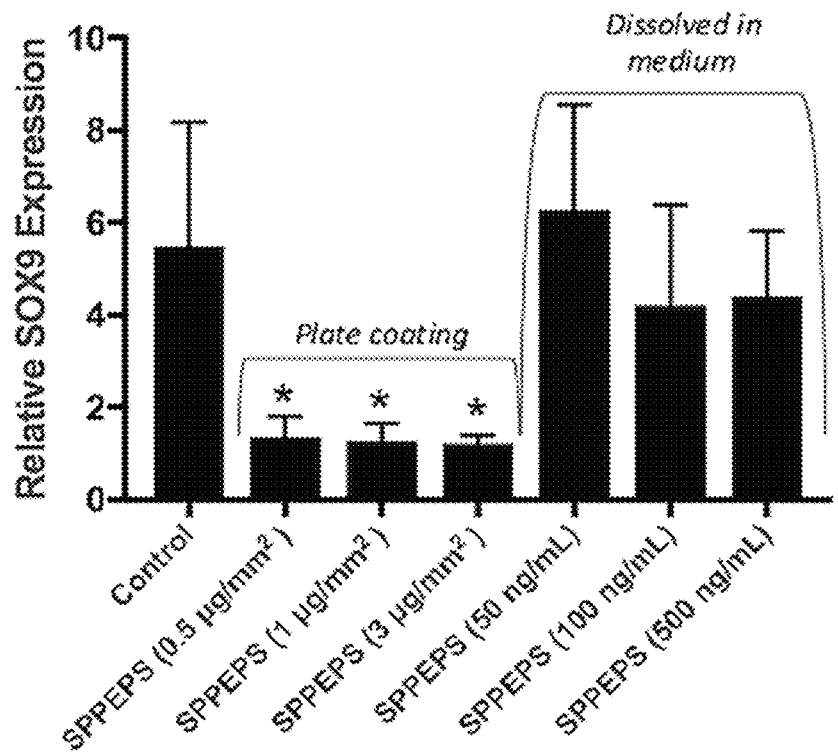
FIG. 2 shows the analysis of Sox9 gene expression of rBMSCs on TCT Plates Measured by rt-PCR after 3 Days treated with various concentrations of SPPEPS (SEQ ID NO:2) peptide. (*)=p<0.05 compared to the control. (n=6).
Figure 3:
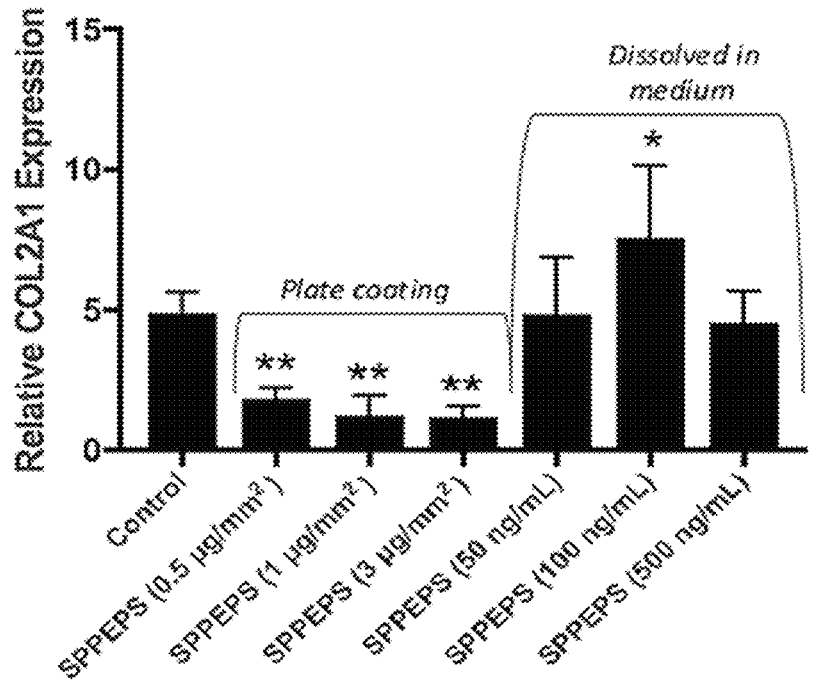
FIG. 3 shows the analysis of collagen type II gene expression of rBMSCs on TCT Plates Measured by rt-PCR after 3 Days treated with various concentrations of SPPEPS (SEQ ID NO:2) peptide. For the SPPEPS (SEQ ID NO:2) 100 ng/ml group, the collagen type II gene expression was 1.5× and 35% higher than the control group. (*)=p<0.05 and (**)=p<0.001 compared to the control. (n=6).
Figure 4:
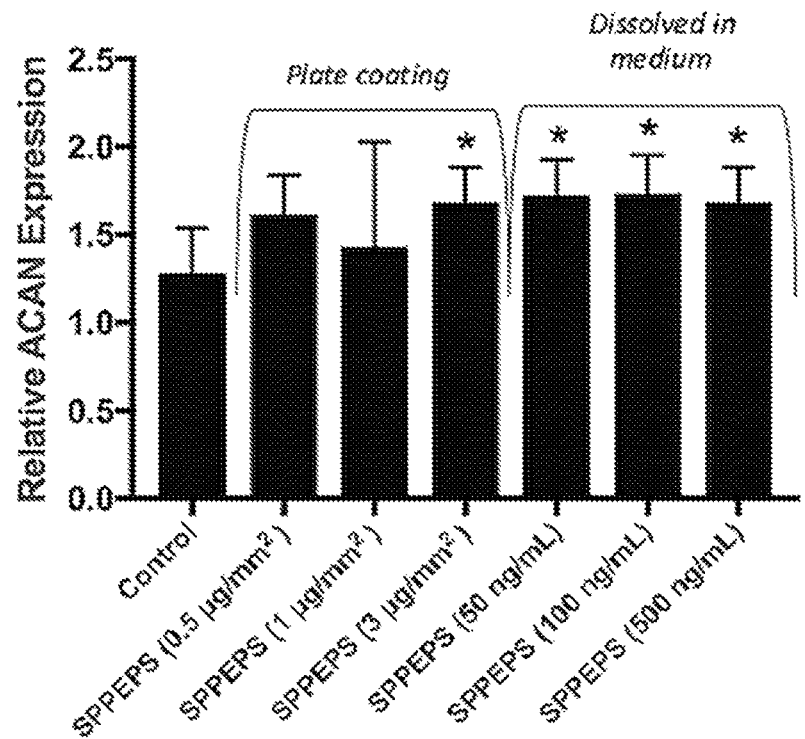
FIG. 4 shows the analysis of aggrecan gene expression of rBMSCs on TCT Plates Measured by rt-PCR after 3 Days treated with various concentrations of SPPEPS (SEQ ID NO:2) peptide. For the SPPEPS (SEQ ID NO:2) 50 ng/ml, 100 ng/ml and 500 ng/ml group, the aggrecan gene expressions were about 1.5× and 35% higher than the control group. (*)=p<0.05 compared to the control. (n=6).

In a preliminary study, the collagen type II gene expression of SPPEPS (SEQ ID NO:2) 100 ng/ml group was 2.3 times higher than in the control group ($p<0.05$), which led us to further analyses on the chondroinductivity of the SPPEPS (SEQ ID NO:2) peptide. For rBMSCs on TCT plates, the Sox9 gene expression from control group was 4.0, 4.2, and 4.5 times higher than all of the coating groups (SPPEPS (SEQ ID NO:2) 0.5, 1 and 3 µg/mm2) respectively (p<0.05). Comparing the Sox9 gene expressions of the peptide groups indicated that the Sox9 gene expression of SPPEPS (SEQ ID NO: 2) 50 and 500 ng/ml groups were 4.5, 4.9 and 5.2 times and 3.2, 3.4 and 3.6 times higher than SPPEPS (SEQ ID NO:2) 0.5, 1 and 3 µg/mm2 groups respectively (p<0.05) (FIG. 2). The collagen type II gene expressions from SPPEPS (SEQ ID NO:2) 0.5, 1 and 3 µg/mm2 and SPPEPS (SEQ ID NO:2) 100 ng/ml groups were 61, 74 and 75% lower and 1.5 times higher than in the control group, respectively (p<0.05). Comparing the relative collagen type II gene expressions of peptide groups indicated that collagen type II gene expressions from peptide in medium groups (SPPEPS (SEQ ID NO:2) 50, 100 and 500 ng/ml) were 2.5 to 6.5 times higher than peptide coating groups (SPPEPS (SEQ ID NO:2) 0.5, 1, 3 µg/mm2) (p<0.05). In addition, collagen type II gene expression from SPPEPS (SEQ ID NO:2) 100 ng/ml group was 1.5 and 1.6 times higher compared to SPPEPS (SEQ ID NO: 2) 50 and 500 ng/mL, respectively (p<0.05) (FIG. 3). The aggrecan gene expressions from SPPEPS (SEQ ID NO:2) 3 µg/mm2, 50, 100 and 500 ng/ml groups were 31, 34, 35, 31% higher compared to the control group respectively (p<0.05) (FIG. 4). There were not any other significant differences among the groups.

Figure 5:
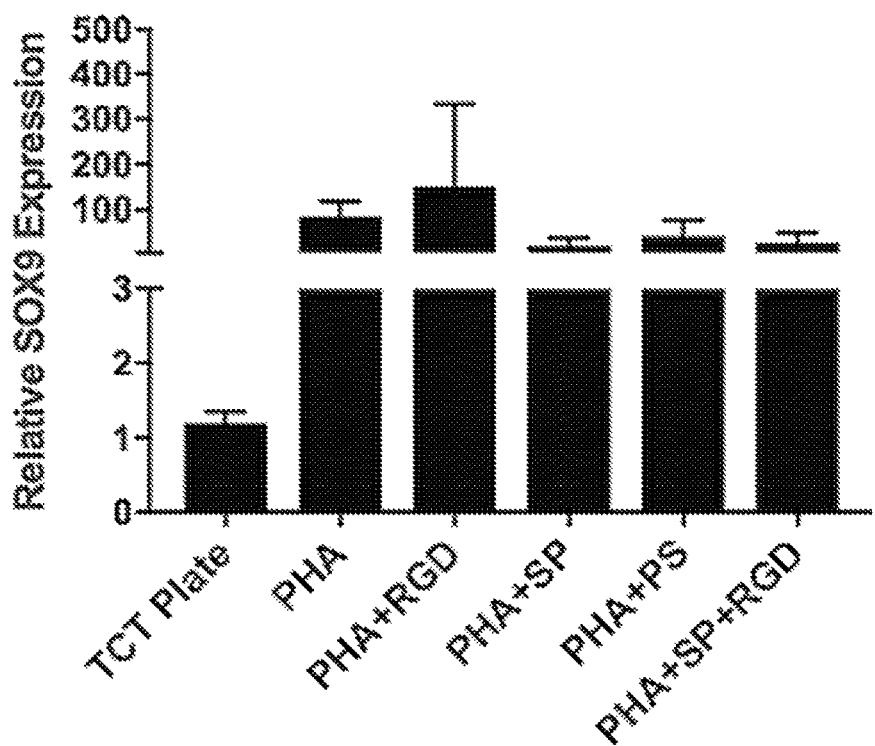
FIG. 5 shows analysis of Sox9 gene expression of rBMSCs on hydrogel surfaces measured by rt-PCR after 3 Days. All treatments showed increased expression of Sox9 after treatment. Treatments were as for the experiments of FIG. 1. (*)=p<0.05 compared to the TCT plate group. (n=4).
Figure 6:
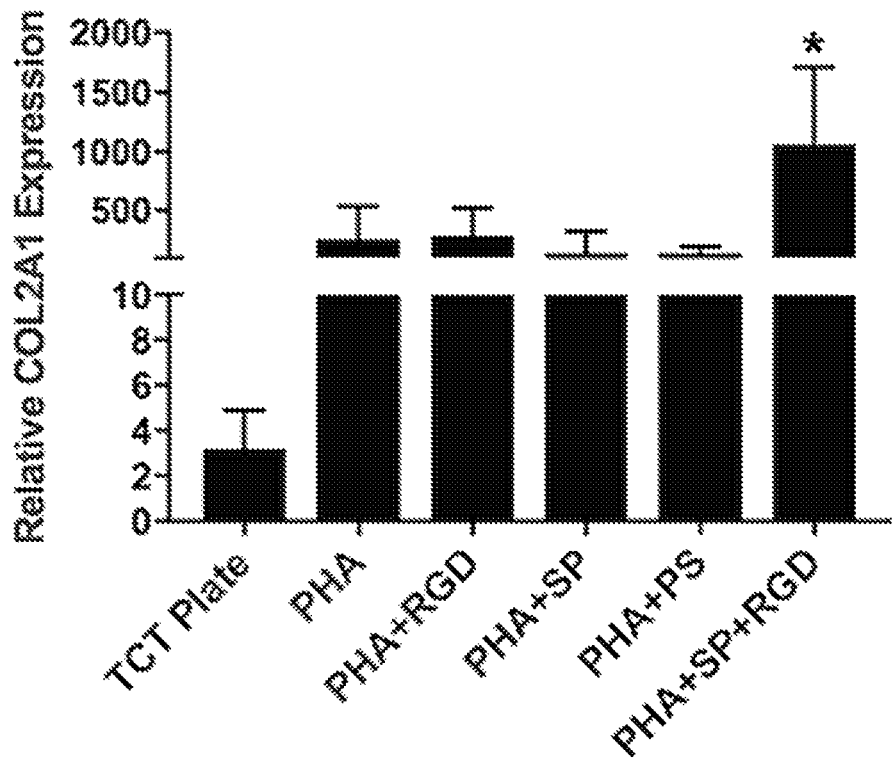
FIG. 6 shows analysis of collagen type II gene expression of rBMSCs on the hydrogel surfaces using the treatments of FIG. 1, measured by rt-PCR after 3 Days. Collagen type II gene expression in the PHA+SP+RGD group was 300 times higher than TCT plate control group and 3 to 7 times higher than PHA, PHA+RGD, PHA+SP and PHA+PS groups. PHA=5% (w/v) pentanoate-functionalized hyaluronic acid with no peptide conjugation. (*)=p<0.05 compared to the TCT plate group. (n=4).
Figure 7:
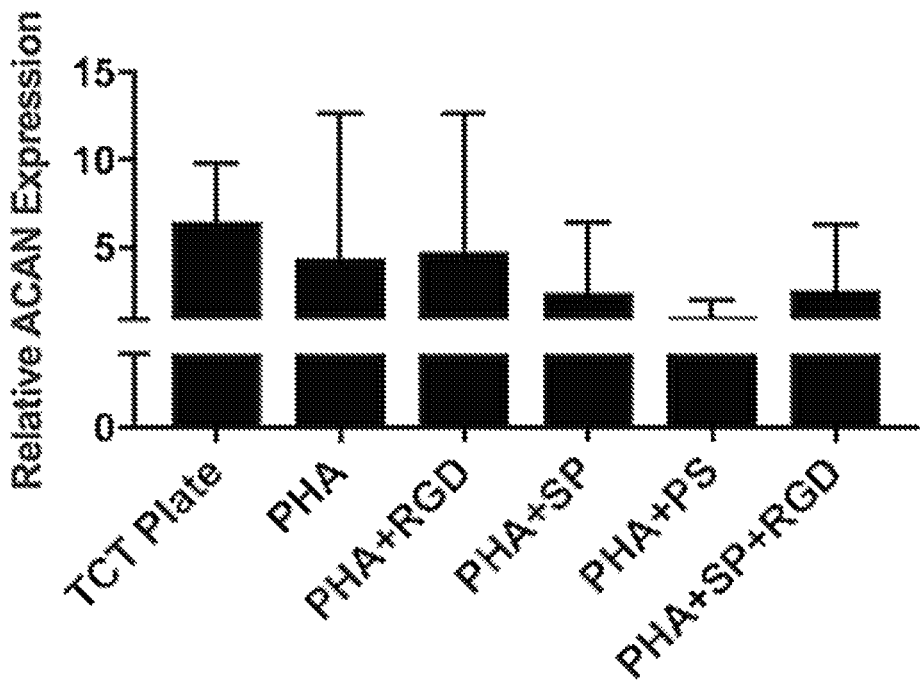
FIG. 7 shows analysis of aggrecan gene expression of rBMSCs on the hydrogel surfaces using the treatments of FIG. 1 measured by rt-PCR after 3 Days. (*)=p<0.05 compared to the TCT plate group. (n=4).

In the hydrogel surfaces study, the Sox9 gene expressions from the hydrogel groups were 20 to 100 times higher than TCT plate group although none of the differences were significant (FIG. 5). The collagen type II gene expression from PHA+SP+RGD group was 300 times higher compared to the TCT plate group and 3 to 7 times higher compare to the PHA, PHA+RGD, PHA+SP and PHA+PS groups, respectively (p<0.05). There were no other significant differences among the collagen type II gene expressions although the collagen type II gene expressions of the PHA, PHA+RGD, PHA+SP and PHA+PS groups were 40 to 90 times higher than TCT plate group (FIG. 6). The aggrecan gene expression of TCT plate group was 2.6 times higher than PHA+PS group (p<0.05). There were no other significant differences among the gene expressions (FIG. 7).

Discussion

Chondroinductivity of the Ser-Pro-Pro-Glu-Pro-Ser (SPPEPS) (SEQ ID NO:2) peptide candidate was investigated with rat bone marrow-derived mesenchymal stem cells (rBMSCs) in 2D culture. The peptide was then conjugated to a pentenoate-functionalized hyaluronic acid (PHA) hydrogel, and the chondroinductivity of the resultant hydrogels (via 2D culture on their surface) was evaluated by real-time quantitative polymerase chain reaction (rt-PCR).

The SPPEPS (SEQ ID NO:2) peptide sequence is derived from the latency-associated protein (LAP) region of transforming growth factor-β3 (TGF-β3). The chondroinductivity of SPPEPS (SEQ ID NO:2) peptide sequence was evaluated by coating SPPEPS (SEQ ID NO:2) peptide onto tissue culture treated (TCT) plates or was dissolved in cell culture medium of rBMSCs with different concentrations. For further analysis, the chondroinductivity of the SPPEPS (SEQ ID NO:2) group was evaluated when the SPPEPS (SEQ ID NO:2) peptide was conjugated to PHA hydrogels and rBMSCs were cultured on top of the hydrogels. The peptide was conjugated to PHA with or without an RGD adhesion peptide.

In the preliminary study and the gene expression analyses of rBMSCs on TCT plates, higher collagen type II gene expressions were recorded when the SPPEPS (SEQ ID NO:2) peptide was dissolved in the cell culture medium (100 ng/ml), which affirmed the reproducibility and self-consistency of the results, in addition, in the gene expression analyses of rBMSCs on the TCT plates aggrecan expression of rBMSCs from the same group (100 ng/mL SPPEPS (SEQ ID NO:2)) was higher than the control group (100 ng/mL SPPEPS (SEQ ID NO:2)). For the groups that had the peptide as the coating of the cell culture plates, aggrecan gene expression was higher than the negative control but the expressions of collagen type II and Sox9 genes were lower compared to all the other groups.

In the hydrogel surface analysis, both Sox9 and collagen type II gene expressions of all the hydrogel groups were 20 to 300 times higher compared to the TCT groups which indicated the high impact of PHA for chondroinductivity whether the peptides were conjugated to the hydrogel or not. Although the differences were not identified as significant (except collagen type II gene expression for PHA+RGD+SP compared to the TCT plate group) in statistical analysis, because of the low sample number in the study, the data still emphasizes the high impact of PHA on chondrogenic differentiation. The collagen type II gene expression for PHA+RGD+SP group was 3 to 7 times higher than all the other PHA groups and 300 times higher than the TCT plate group (p<0.05), which demonstrates that a synergistic effect of the adhesion peptide (RGD) and the chondroinductive peptide (SPPEPS (SEQ ID NO: 2)) provided an environment for rBMSCs which further encouraged the chondrogenic differentiation.

Example 2

The goal of this experiment was to determine if a biomaterial comprising the chondroinductive peptide SPPEPS (SEQ ID NO:2) could induce hyaline-like cartilage production by guiding chondrogenic differentiation of endogenous bone marrow-derived mesenchymal stem cells (BMSCs) without the need to harvest/seed cells of any kind or to incorporate any growth factors. Our hypothesis was that the SPPEPS (SEQ ID NO:2) peptide in PHA hydrogels would lead to a more hyaline-like cartilage tissue compared to PHA hydrogels alone. In this example, thiolated RGD or thiolated SPPEPS (SEQ ID NO:2) peptides were conjugated to PHA. In addition, hyaluronic acid nanoparticles (HAnp) were incorporated into the hydrogels to increase the hydrogel precursor yield stress for surgical placement. The performance of the PHA hydrogels with conjugated SPPEPS (SEQ ID NO:2) were compared in regeneration of rabbit femoral condylar cartilage defects to PHA hydrogels alone (negative control) and to PHA hydrogels conjugated with the well-known RGD adhesion peptide. The resultant hydrogels were implanted into defects in the femoral condylar cartilage of rabbits then photocrosslinked by exposure to UV light. After 12 weeks, although differences in gross morphological scoring were not statistically significant, the SPPEPS (SEQ ID NO:2) peptide treatment group did indicate induction of chondrogenic differentiation based on strong collagen II immunostaining and cell morphology relative to a PHA only control. The collagen II production and evidence of rudimentary columnar organization of chondrocyte-like cells in lacunae in the SPPEPS (SEQ ID NO:2) group supported the use of the disclosed compounds as synthetic chondroinductive peptides for orthopedic regenerative medicine.

Materials and Methods

Synthesis of Hyaluronic Acid Nanoparticles (HAnp)

HAnp were made by utilizing carbodiimide crosslinking chemistry. Briefly, 300 mg HA (MW=16 KDa, Lifecore Biomedical, Chaska, MN) was dissolved in 120 mL DI water, and then after the HA was fully dissolved, 200 mL acetone was added. 60 mg adipic acid dihydrazide (AAD) and 140 mg 1-Ethyl-3-[3-dimethylaminopropyl] carbodiimide hydrochloride (EDC) (Thermo Scientific, Rockford, IL) were each dissolved in 1 mL DI water and were then added to the solution after 15 and 10 minutes, respectively. After 20 minutes, 200 mL acetone was added to the solution. The reaction was completed in 3 hours. The solution was dialyzed against DI water for 2 days, frozen, lyophilized and stored at −20° C. Synthesis of Pentenoate Functionalized Hyaluronic Acid (PHA)

PHA was prepared as described previously. Briefly, 5% (w/v) solution of HA (MW=60 KDa, Lifecore Biomedical) in DI water was prepared, DMF was added to the solution to reach a water to DMF ratio of 3:2 while pentenoic anhydride (Cat #471801, Sigma-Aldrich, St. Louis, MO) was slowly added to the solution in 5 M excess relative to HA. The pH of the solution was monitored for 5 hours and was maintained at pH 8-9 by adding 1M NaOH to the solution. The reaction was completed overnight. NaCl was added to the solution to reach 0.5M concentration of NaCl, and the polymer precipitated by adding 4 volumes of acetone and centrifuging for 5 minutes (7,000×g). The precipitated PHA was dissolved in DI water and dialyzed for 48 hours. The final product was 17% functionalized with the pentenoate group in relation to the repeating disaccharide unit. Functionalization was confirmed with $^1$H-NMR (Varian Mercury VNMRS 500 MHz spectrometer, see FIG. 16 in U.S. Ser. No. 62/723,674) by comparing the integration of the alkene peaks on the functional group to the acetyl methyl group on the HA. PHA was frozen, lyophilized, and stored at −20° C.

Hydrogel Preparation

The hydrogel precursor material was prepared the day before the surgery. PHA was sterilized using ethylene oxide gas (AN74i, Anderson Anprolene, Haw River, NC). A solution of 2.3 mM 2-Hydroxy-4'-(2-hydroxyethoxy)-2-methylpropio-phenone (Irgacure 2959, Cat #410896, Sigma-Aldrich) and 1% dithiothreitol (DTT, Cat #D0632, Sigma-Aldrich) was prepared in phosphate-buffered saline (PBS) and was sterile-filtered. To prepare the hydrogels in the PHA group, PHA and HAnp were added to the PBS solution to make a 5% (w/v) concentration of each. To incorporate peptides (i.e., SPPEPS (SEQ ID NO:2) or RGD) in the hydrogel network, a solution with concentration 2% (w/v) PHA and 5% (w/v) HAnp was made by adding PHA and HAnp to PBS solution containing 1 mM Irgacure and 1.5 mM thiolated SPPEPS (SEQ ID NO:2) or thiolated RGD. The solutions were fully dissolved (2 hours) and the peptides were conjugated to the PHA after exposure to 312 nm UV light (EB-160C, Spectroline) for 2 minutes. Afterward, the solutions were mixed with additional PHA and PBS solution containing Irgacure and DTT to achieve the final concentrations of 5% (w/v) PHA, 2 mM Irgacure and 1% DTT. When the PHA and HAnp were completely dissolved (2 hours), the solutions were pipetted into sterile syringes, protected from light with tin foil, and kept sterile until the surgery. Thiolated peptides were custom-ordered (Biosynthetic, Lewisville, TX) and synthesized on a PTI Symphony peptide synthesizer (Tucson, AZ). Each peptide's purity was shown to be >95% using analytical high-performance liquid chromatography (HPLC, Shimadzu, Columbia, MD).

Description of Experimental Groups

Four different study groups were investigated (n=6). In all the groups, defects were created in the medial femoral condyles, and three holes were microdrilled into the subchondral bone (Table 3). In the sham control group, no material was placed in the defect. The other groups were the PHA, PHA+RGD and PHA+SP groups (i.e., 5% PHA+5% HAnp, 5% PHA+5% HAnp containing 1.5 mM RGD, and 5% PHA+5% HAnp containing 1.5 mM SPPEPS (SEQ ID NO:2), respectively).

TABLE 3

List of Group Placement and Outcome Analysis for Each Rabbit Knee

| Animal no | Left Knee | Right Knee | Time (Weeks) | Analysis |
|---|---|---|---|---|
| Rabbit 1 | Control | PHA | 12 | Morphology and histology |
| Rabbit 2 | PHA + RGD | Control | 12 | Morphology and histology |
| Rabbit 3 | Control | PHA + SP | 12 | Morphology and histology |
| Rabbit 4 | PHA | PHA + SP | 12 | Morphology and histology |
| Rabbit 5 | PHA + RGD | PHA | 12 | Morphology and histology |
| Rabbit 6 | PHA + SP | PHA + RGD | 12 | Morphology and histology |
| Rabbit 7 | PHA | PHA + SP | 12 | Morphology and histology |
| Rabbit 8 | PHA + RG | PHA | 12 | Morphology and histology |
| Rabbit 9 | PHA + SP | PHA + RGD | 12 | Morphology and histology |
| Rabbit 10 | Control | PHA | 12 | Morphology and histology |
| Rabbit 11 | PHA + RGD | Control | 12 | Morphology and histology |
| Rabbit 12 | Control | PHA + SP | 12 | Morphology and histology |

Surgical Procedure

Figure 8:
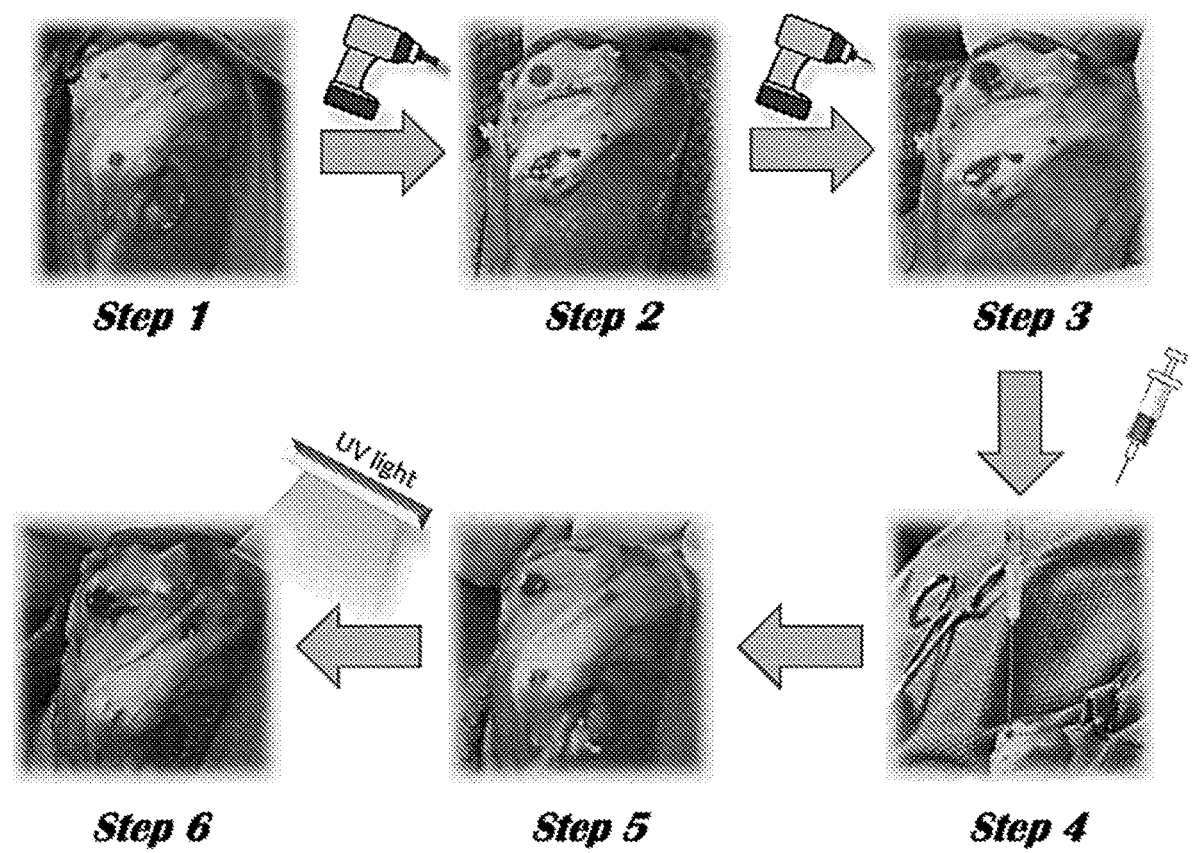
FIG. 8 shows the sequence of steps used in a surgical procedure used in the in vivo experiments of Example 2. (1) Pilot hole (1 mm diameter) was created in the femoral condylar cartilage. (2) The hole was enlarged to 3.5 mm diameter. (3) Microdrilling of 4 holes (0.4 mm in diameter) in the subchondral bone stimulated bone marrow to the defect area. (4 and 5) The hydrogel precursor was implanted in the defect with needle and syringe. (6) The hydrogel was exposed to UV light for 5 minutes for cross-linking.

All animal experiments were approved by the Institutional Animal Care and Use Committee of the University of Oklahoma Health Sciences Center (Protocol #17-007-SS A). 12 female New Zealand white rabbits, each 6 months old and between 4 to 4.5 kg (Robinson Service, Inc (RSI), Mocksville, NC), were monitored for normal and healthy behavior a week prior to the surgery. Following analgesic delivery, stable general anesthesia, and antibiotic administration, the area around each knee was shaved and prepared (including 3 rounds of alternating chlorhexidine scrub and alcohol solution with a final betadine spray). Before the procedure, lactated ringers injection (LRS) was provided at multiple injection sites around the neck and shoulders to ensure proper hydration and to maintain blood pressure. After surgical anesthesia was established, the rabbits were laid in the supine position and a medial parapatellar incision was made sufficient to allow exposure of the medial femoral condyle. The tibia was lightly pushed to displace it laterally to allow the exposure of the medial femoral condyle, and an osteochondral defect of 3.5 mm diameter was drilled in the medial femoral condyle cartilage with the depth of 1-2 mm, essentially a full-thickness cartilage defect that penetrated into subchondral bone. An initial pilot defect was created with a 1 mm drill bit, and gradually enlarged to a 3.5 mm defect using 2 and 3.5 mm drill bits. The joint was washed of debris with sterile saline before three smaller holes (0.4 mm diameter) were microdrilled into the subchondral bone of the defect area to mobilize local bone marrow to the site of cartilage lesion. Before placing the hydrogels into the defect, the blood in the defect was removed with sterile gauze. The hydrogel precursor material was placed in the defect area with a syringe and a needle and exposed to 312 nm UV-light at 9 mW/cm² (EB-160C, Spectroline) for 5 minutes to form a crosslinked network (FIG. 8). The joints were washed with sterile saline, and the articular capsule and bursae were closed with absorbable suture before binding of the skin with intradermal absorbable suture. The rabbits were placed on a recirculating hot water blanket during anesthesia and recovery and use of analgesic agents continued for 3 days after the surgery. Rabbit sternal recumbency was monitored until they could rest unassisted in their home cage.

Post-Surgical Care

After both knee procedures were finished, rabbits were returned to their cages and their knee joints were allowed unconstrained post-operative movement. Each rabbit's condition was monitored to detect post-operative complications. Animals were examined three times a day for the first 3 days, once a day for 7 days, and every other day for the remaining 10.5 weeks to ensure that they exhibited normal patterns of behavior, were active and inquisitive, had normal posture and movements, and were eating and drinking. Physical examinations were performed to look for signs of infection or distress. All the rabbits displayed normal behavior one day after the surgery and no signs of inflammation were observed, except for rabbit #04, who had inflammation of the left knee (PHA group) after surgery, but fully recovered within 5 days.

Gross Morphological Assessment

The animals were euthanized after 12 weeks by intravascular administration of concentrated barbiturate (200 mg/kg) in an ear vein after isoflurane anesthesia via masking (as approved by the IACUC protocol). The depth of anesthesia was analyzed by measuring heart rate, respiration rate, and pedal withdrawal. After the joint retrieval, the knees were photographed. Gross morphology was assessed from the images by three independent scorers. The scoring criteria were developed from the ICRS scoring chart (Table 4), based on edge integration of the boundaries of regenerated tissue and native cartilage, smoothness of the repair surface, degree of filling at the cartilage surface, color of the regenerated cartilage, and the percent of repair tissue relative to the total area.

TABLE 4

Scoring Table for Morphological Analysis

| Feature | Score |
|---|---|
| Repair tissue or test article present in implant site | |
| Full presence | 2 |
| Partial | 1 |
| None | 0 |
| Edge integration (New tissue relative to native cartilage) | |
| Full | 2 |
| Partial | 1 |
| None | 0 |
| Smoothness of repair surface | |
| Smooth | 2 |
| Intermediate | 1 |
| Rough/Missing | 0 |
| Cartilage surface degree of filling | |
| Flush | 2 |
| Slight Depression | 1 |
| Depressed/Overgrown | 0 |

TABLE 4-continued

Scoring Table for Morphological Analysis

| Feature | Score |
|---|---|
| Color of cartilage (opacity/translucency of repair tissue) | |
| Translucent | 2 |
| Opaque | 1 |
| Missing | 1 |
| Amount of repair tissue relative to total area of defect (estimated) | % present in defect |

Histological Preparation and Staining

After joint retrieval, knees were placed in formalin for 36 hours and then decalcifying solution for 48 hours (Cat #P7589, Richard-Allan Scientific™ Decalcifying Solution, Thermo Fisher Scientific, Waltham, MA), before samples were washed in running water for 1 hour. The embedding, sectioning, and staining of tissue was performed by the Tissue Pathology Core at the University of Oklahoma Health Sciences Center. Briefly, the tissues were embedded in paraffin and sectioned to a thickness of 4 to 8 μm before mounting on positively charged slides. The slides were dried overnight at room temperature and incubated at 60° C. for 45 minutes. Staining with Hematoxylin & Eosin or Alcian Blue (Cat #3801571, 3801616, 38016SS3DG, Leica Biosystems, Wetzlar, Germany) was performed utilizing a Leica ST5020 Automated Multistainer following manufacturer protocols. The stains were scored blindly by three different scorers base on the grading system described in Table 5.

TABLE 5

Histology Grading System

| Feature | Feature |
|---|---|
| Cellular morphology | |
| Hyaline cartilage | 4 |
| Mostly hyaline cartilage | 3 |
| Mixed hyaline and fibrocartilage | 2 |
| Mostly fibrocartilage | 1 |
| Some fibrocartilage and mostly nonchondrocytic cells | 0 |
| Staining | |
| Normal to nearly normal | 3 |
| Moderate | 2 |
| Slight | 1 |
| None | 0 |
| Cartilage thickness | |
| Similar to the surrounding cartilage | 3 |
| Greater than the surrounding cartilage | 2 |
| Less than the surrounding cartilage | 1 |
| No cartilage | 0 |
| Reconstruction of subchondral bone | |
| Normal | 3 |
| Reduced subchondral bone reconstruction | 2 |
| Minimal subchondral bone reconstruction | 1 |
| No subchondral bone reconstruction | 0 |
| Edge integration | |
| Bonded at both ends of graft | 2 |
| Bonded at 1 end or partially at both ends | 1 |
| Not bonded | 0 |

Immunohistochemistry

The slides were processed similar to the basic histology as described above up through incubation in 60° C. for 45 minutes. The slides were cleared with xylene for 10 minutes and slowly rehydrated in 100%, 95%, and 70% ethanol for 4, 3, and 3 minutes respectively. After incubating the slides in distilled water (dH$_2$O) for 3 minutes, the sections were exposed to 0.3% hydrogen peroxide solution (Cat #ab94666, Abcam, Cambridge, MA) for 30 minutes to suppress endogenous peroxidase activity. The slides were soaked in PBS+ Tween (Cat #P3563, Sigma Aldrich, St Louis, MO) for 5 minutes and were incubated in proteinase K (Cat #ab64220, Abcam) for 15 minutes in 37° C. and 10 minutes in room temperature and then were soaked in PBS tween for 5 minutes. Sections were blocked first with a sequence of Avidin and then Biotin blocking solutions (Cat #SP-2001, Vector Laboratories, Burlingame, CA) each 15 minutes, and then with 3% blocking horse serum (Cat #S-2012, Vector Laboratories) for 20 minutes. The collagen type II primary antibody (Cat #08631711, MP Biomedicals, CA, USA, dilution 1:150) incubation followed for 1 hour at room temperature and then overnight at 4° C. The next day, the slides were soaked in PBS+Tween for 5 minutes and were exposed to horse anti-mouse IgG biotinylated secondary antibody and ABC reagent (Cat #PK-6102, Vector Laboratories) for 60 and 30 minutes, respectively. Visualization was accomplished with ImmPact DAB peroxidase substrate (Cat #SK-4100, Vector laboratories) followed by exposure to DAB enhancing solution (Cat #H2200, Vector laboratories) and then Hematoxylin QS solution (Cat #H-3404, Vector Laboratories) for 10 seconds and 1 minute, respectively. The slides were dehydrated in graded ethanol, cleared in xylene and mounted (Permount, SP15-500 Fair Lawn, NJ).

Statistical Analyses

The data are shown as mean±standard deviation where applicable. The statistical analyses were performed using ANOVA followed by Tukey's HSD method for comparisons (Graphpad Software Inc., La Jolla, CA), the statistical significance threshold was 0.05 in all the analyses (i.e., p<0.05).

Results

Gross Morphological Observations

Figure 9:
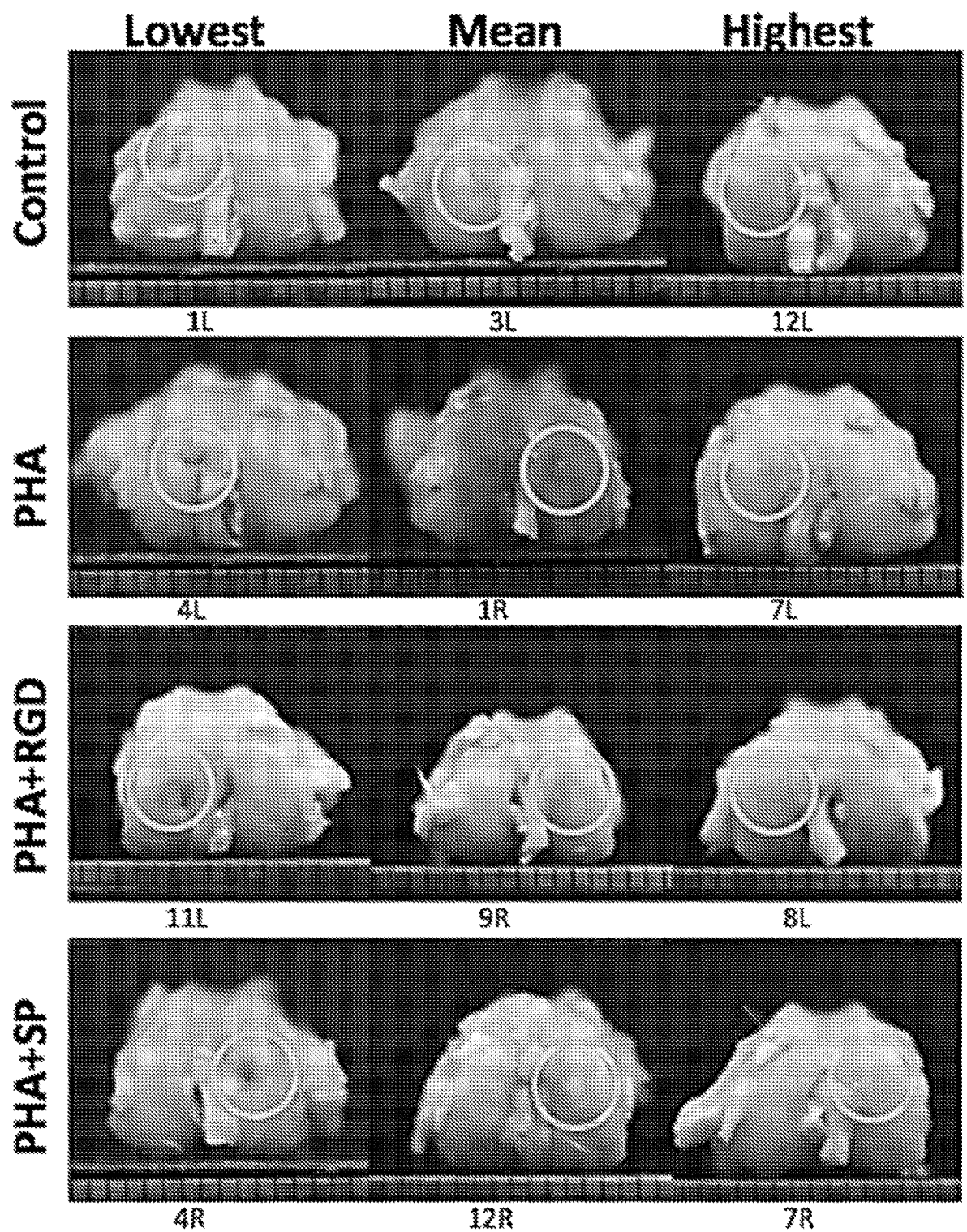
FIG. 9 shows representative images of gross morphology taken after the surgical procedure of Example 2. The images represent the worst, intermediate and best gross morphology of rabbit condyle defects 12 weeks post-surgery. For all the groups, we observed variability in the regenerated tissues; however, the best PHA+RGD sample regenerated the tissue most similar in appearance to the healthy cartilage. Control=The defect with no implanted material, PHA=5% pentanoate-functionalized hyaluronic acid+5% hyaluronic acid nanoparticles, PHA+RGD and PHA+SP are as for FIG. 1. The text under each image represent rabbit number and knee side. (e.g., 1R=Rabbit #1, right knee). Each interval on the rulers indicates 1 mm.
Figure 10:
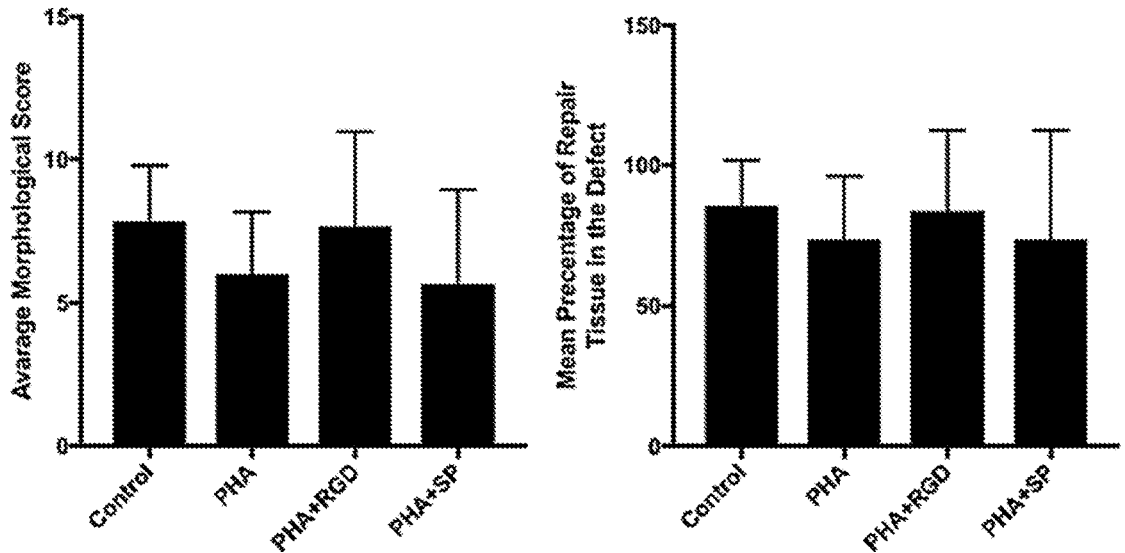
FIG. 10 shows average morphological score (max score=10), and mean percentage of repaired tissue in rabbit condyle defects 12 weeks post-surgery (n=6) in Example 2. Only two condyles scored 10 for average morphological and had 100% regenerated tissue and both the were from the PHA+RGD group. No significant differences were observed among the groups. Control=the defect with no implanted material, PHA=5% pentanoate-functionalized hyaluronic acid+5% hyaluronic acid nanoparticles, PHA+RGD and PHA+SP are as for FIG. 1.

At the time of tissue retrieval, visual inspection revealed no signs of inflammation, swelling, or redness at the defect sites and joint surfaces (FIG. 9). The percentage of the repaired tissue for the control group was between 56 and 100% (average 86±16%), between 30 and 98% for the PHA group (average 74±22%), between 26 and 100% (average 84±26%) for the PHA+RGD group, and between 15 and 100% (average 74±35) for the PHA+SP group. No statistically significant differences were detected among the groups (FIG. 10). The gross morphological scores (FIG. 10), where 10 represents the highest quality of regeneration (Table 3), were between 4 and 9 (average 7.8±1.9) for the control group, between 2.6 and 8.6 (average 6.2±2.1) for the PHA group, between 1.6 and 10 (average 7.6±3.2) for the PHA+RGD group, and between 1.3 and 8.6 (average 5.6±3.2) for the PHA+SP group. PHA+RGD was the only group that had condyles (6R and 8L) with a total score of 10 out of 10 for gross morphology.

Histomorphometric Observations

Figure 12:
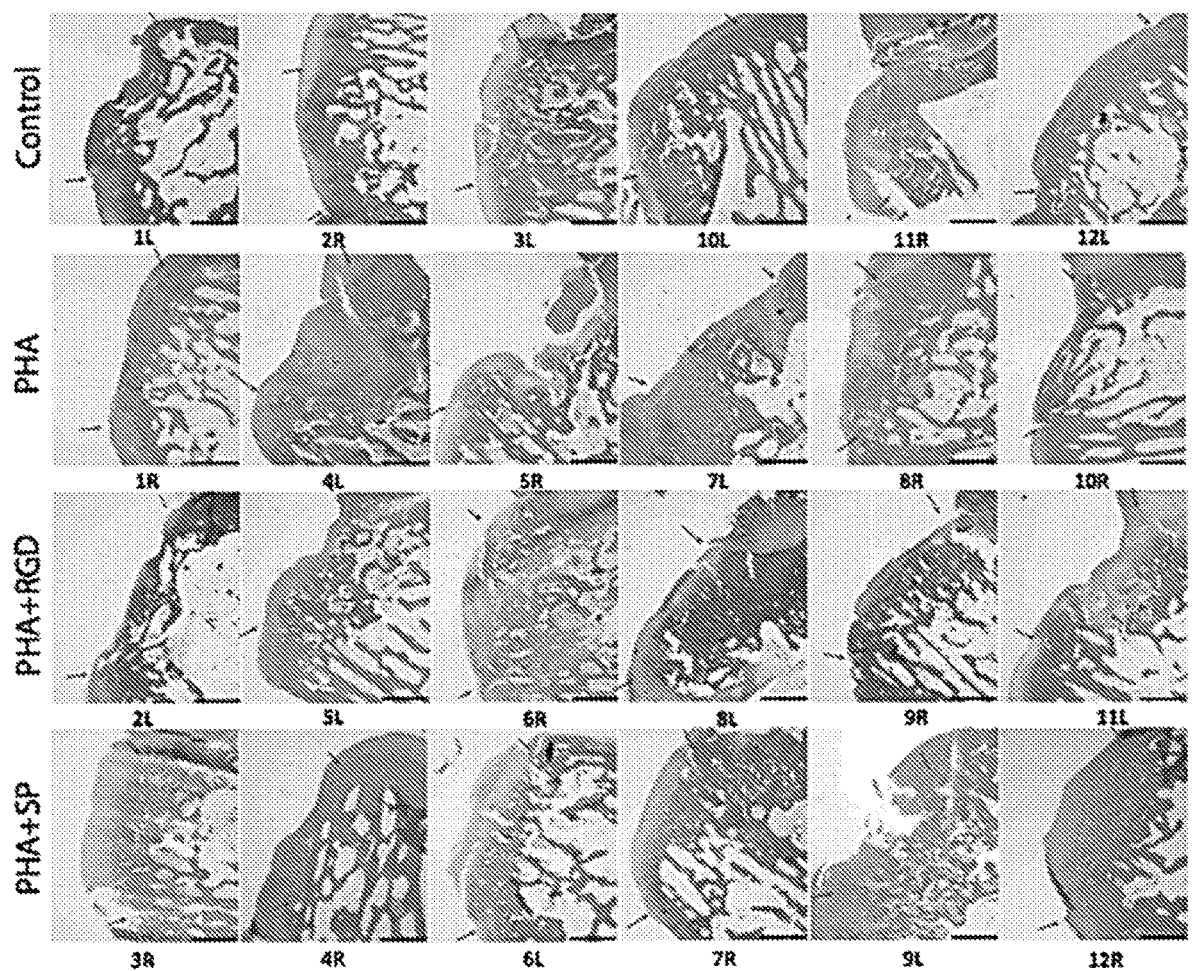
FIG. 12 shows results of histological analysis of rabbit condyle defects at 12 weeks post-surgery (n=6). Sections were taken in the frontal plane and were stained with hematoxylin and eosin (H&E). The microscopic observations indicated the structural variability of the regenerated tissue within all the groups; however, we observed that incorporation of the peptides (PHA+SP and PHA+RGD groups) elevated the structural integrity compared to the PHA group. Control=The defect with no implanted material, PHA=5% pentanoate-functionalized hyaluronic acid+5% hyaluronic acid nanoparticles, PHA+RGD and PHA+SP are as for FIG. 1. The text under each staining represent rabbit number and knee side. (e.g., 1R=Rabbit #1, right knee) The arrows are pointed at the edges of the defects. Scale bars=1 mm.

The morphometric analyses of the H&E staining (FIG. 12) indicated that in 50% of the condyles from the control group, the cells were mostly chondrocytes, 33% of the defects had mixed chondrocytes and fibrocartilage differentiated in the cartilage zone and 17% had mostly fibrocartilage appearance. For the PHA group, we observed that 17% of the defects had mostly chondrocytes, 50% had mixed chondrocytes and fibrocartilage and 33% had mostly fibrocartilage. In the PHA+RGD group, for 17% of the condyles, most of the cells in the defects were chondrocytes; for 67% of the defects, the cells were a mix of fibrocartilage and chondrocytes; and 17% of the defects mostly had a fibrocartilage appearance. In the PHA+SP group, the cells were mostly chondrocytes in 33% of the defects. We observed a mix of fibrocartilage and chondrocytes in 50% of the defects, and mostly fibrocartilage in 17% of the defects.

The scoring of the cartilage thicknesses indicated that the cartilage thicknesses of 17% of the condyles from the control group were similar to the surrounding native cartilage, for 50% and 33% of the condyles the cartilage thicknesses were greater and less than the healthy cartilage, respectively. For the PHA group 33% of the condyles showed no cartilage thickness, 17% had greater cartilage thicknesses compared to the surrounding tissue, and 50% had smaller cartilage thicknesses compared to the surrounding. The cartilage thicknesses in the defect areas of PHA+RGD condyles were greater than the surrounding for 50% of the defects and less than the surrounding cartilage for the rest. 17% of the condyles from the PHA+SP group had cartilage thicknesses similar to the surrounding cartilage. The cartilage thicknesses were greater and less than the surrounding cartilage for 17% and 66% of the condyles, respectively.

In the condyles of the control group, 66%, 17%, and 17% had edge integrations on both ends, on one end, and on neither end, respectively. In the PHA group, 33%, 50%, and 17% of the condyles had cartilage integrations on both ends, on one end, and on neither end, respectively. The integrations of the regenerated tissues were at the both ends for 33% and at one end for 67% of the knees for PHA+RGD condyles. 50% of the defect integrations were at both sides and the rest were integrated on one side in the PHA+SP condyles.

The scoring of the regenerated subchondral bone in the defect areas indicated that 50% of the condyles from the control group showed normal subchondral bone regeneration. 33% and 17% of the condyles had reduced and minimal reconstruction of subchondral bone compared to the native surrounding tissue, respectively. In the PHA group, 33% of the samples showed no subchondral bone reconstruction, 17% of the condyles had normal reconstruction of subchondral bones compared to the surrounding tissue, and 50% of them showed no reconstruction of the subchondral bone. In the PHA+RGD group, 17%, 50%, and 33% of the condyles had normal, reduced, and minimal reconstruction of subchondral bones, respectively. In the PHA+SP group, for 50% of the condyles, the reconstruction of the subchondral bones appeared normal, and for the rest of the knees the reconstructed bones were reduced compared to the surrounding tissue.

Figure 11:
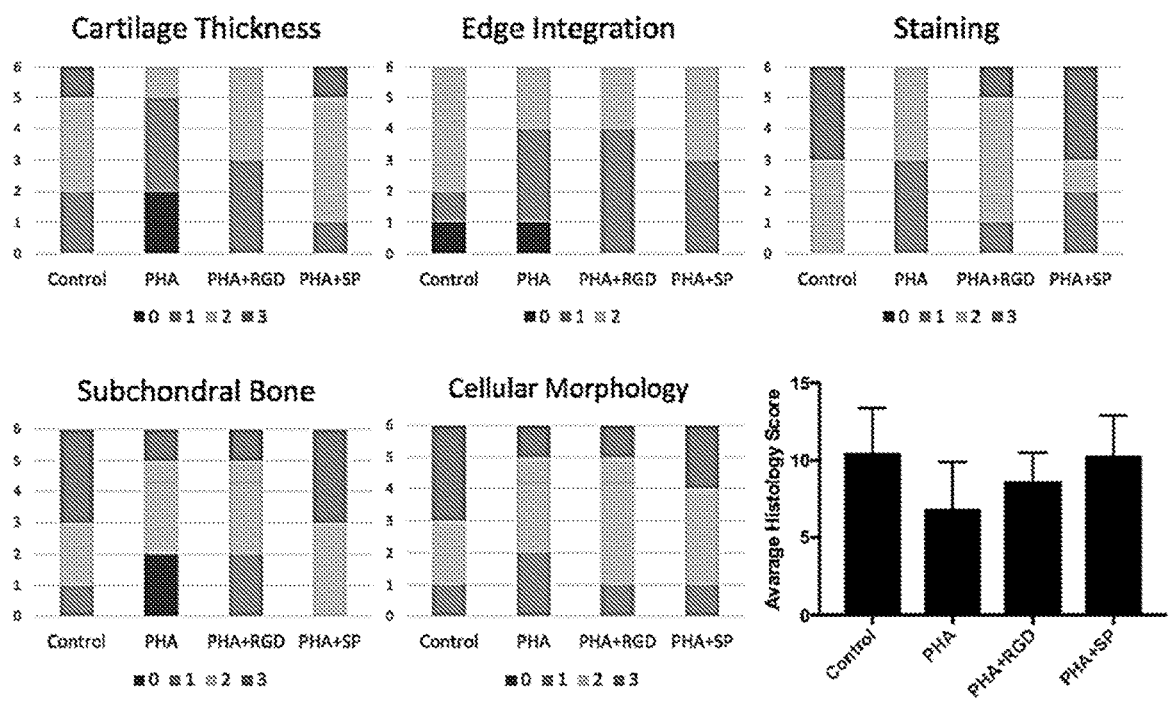
FIG. 11 shows a histology score distribution of the results from Example 2. Stacked column plot compared each of the histological scores and the average histology score for each group, values represent mean+standard deviation (n=6). The histology scoring system is explained in Table 3. There was a more frequent presence of the high score (e.g., 3) for the PHA+SP and Control groups, and there were no examples of "0" score for either of the peptide groups. Control=The defect with no implanted material, PHA=5% pentanoate-functionalized hyaluronic acid+5% hyaluronic acid nanoparticles, PHA+RGD and PHA+SP are as for FIG. 1.
Figure 13:
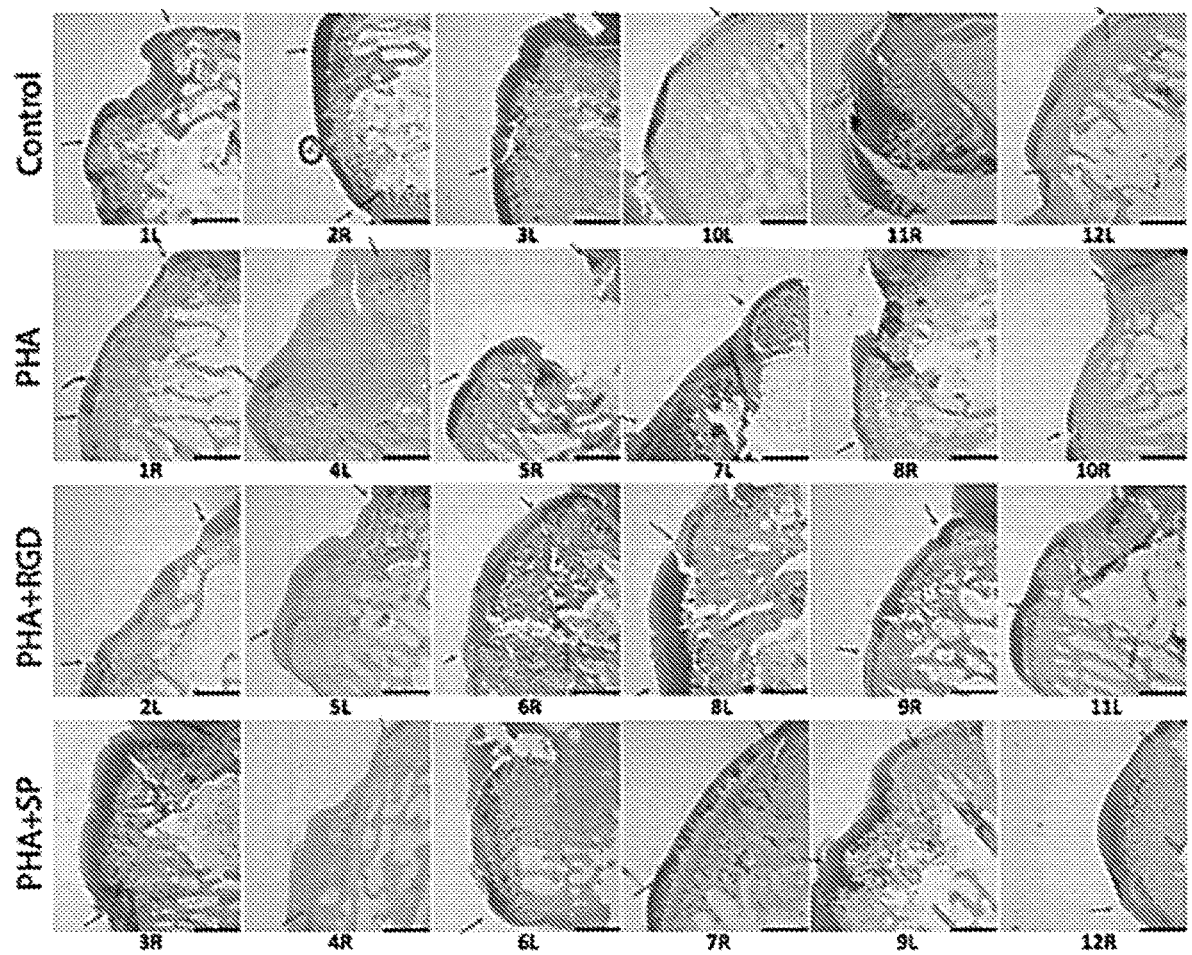
FIG. 13 shows histological analysis of rabbit condyle defects at 12 weeks post-surgery (n=6). Sections were taken in the frontal plane and were stained with Alcian Blue. The stain intensities were superior in the control and PHA+SP group compared to the other groups. Control=The defect with no implanted material, PHA=5% pentanoate-functionalized hyaluronic acid+5% hyaluronic acid nanoparticles, PHA+RGD and PHA+SP are as for FIG. 1. The text under each staining represent rabbit number and knee side. (e.g., 1R=Rabbit #1, right knee). Arrows indicate the edges of the defects. Scale bars=1 mm.

In the control group, the Alcian Blue staining of the knees was intense for the 2R, 3L and 11R condyles, whereas the regenerated cartilage in the 1L, 10L and 12R condyles did not stain intensely (FIG. 13). From the morphometric score distribution (FIG. 11), we observed that 50% of the knees were normally stained and 50% were moderately stained. In the PHA group, we did not observe any intense Alcian Blue staining, 50% of the condyles had moderate staining and 50% of them had slight staining. In the Alcian Blue staining of the PHA+RGD group, we observed that the 8L condyle had normal staining (i.e., similar to healthy tissue) in the defect area and the rest of the condyles had slight or moderate staining. The scoring of the PHA+SP group indicated that 50% of the condyles had normal staining, 17% of them had moderated and 33% had slight staining.

Collagen II Immunostaining

Figure 14:
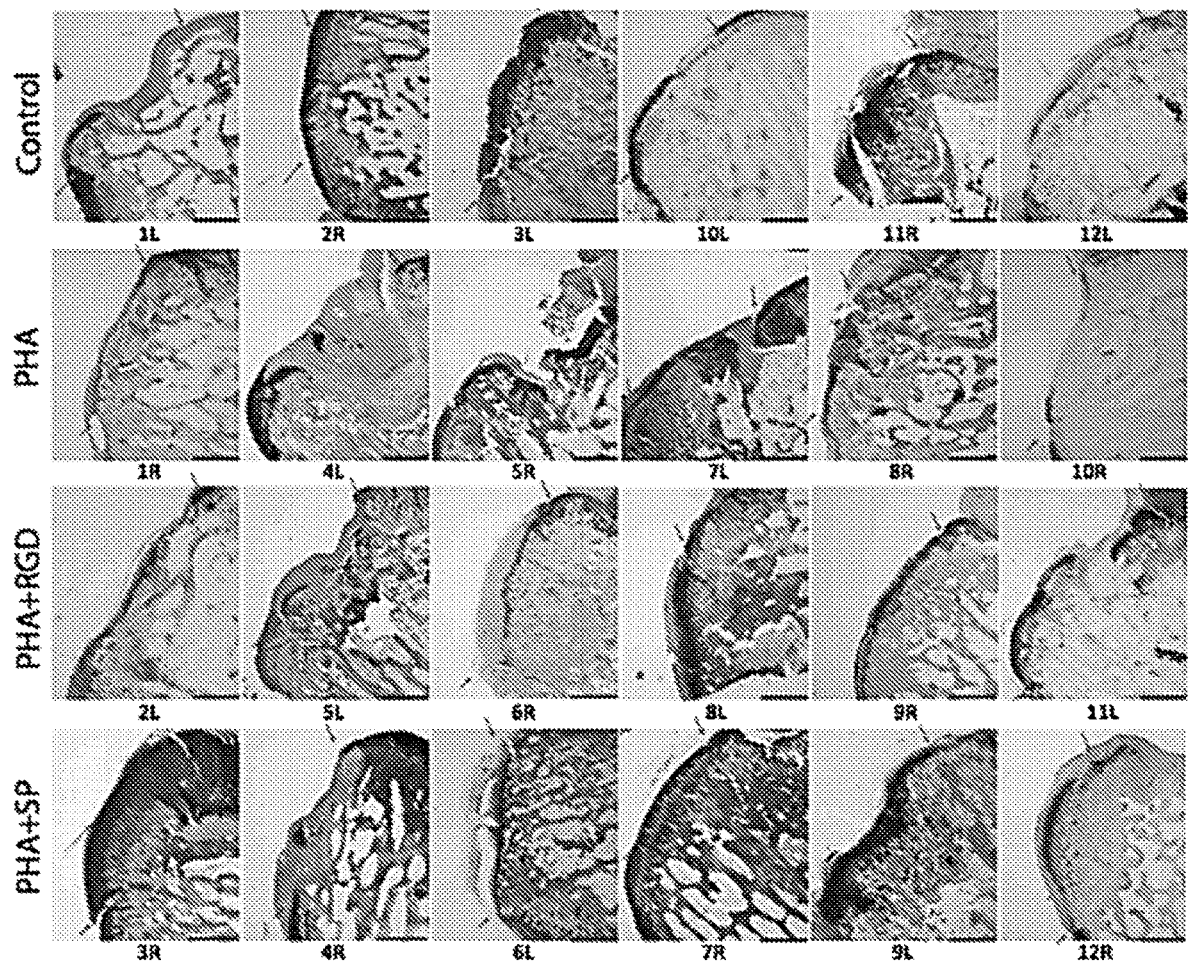
FIG. 14 examines the Collagen II Immunohistochemistry of rabbit condyle defects at 12 weeks post-surgery (n=6) for Example 2. Sections were taken in the frontal plane and were stained with collagen type II antibody. 3R, 7R and 9L condyles from PHA+SP group and 2R condyles from Control showed the most intense and prevalent collagen II staining, which indicated the superior potential of the PHA+SP group in collagen type II production. Control=The defect with no implanted material, PHA=5% pentanoate-functionalized hyaluronic acid+5% hyaluronic acid nanoparticles, PHA+RGD and PHA+SP are as for FIG. 1. The text under each staining represent rabbit number and knee side. (e.g., 1R=Rabbit #1, right knee). The arrows are pointed at the edges of the defects. Scale bars=1 mm.
Figure 15:
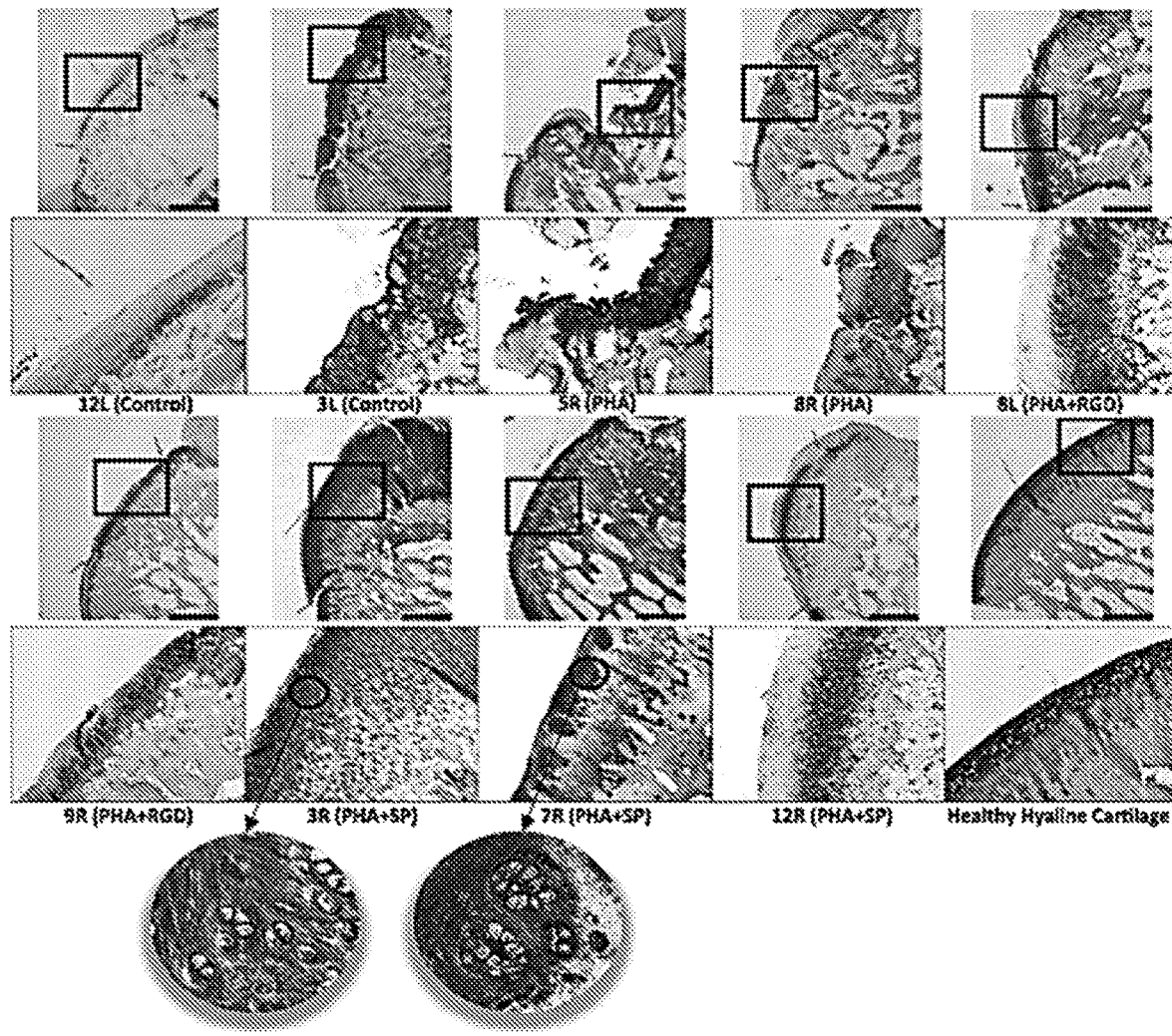
FIG. 15 show histological sections which represent magnified collagen II of the animals in Example 2 after 12 weeks post-surgery (n=6). Sections of rabbit condyle defects were taken in the frontal plane and were stained with collagen type II antibody. Magnified images shown below each overall section correlate to the box above. The magnified image of 3L condyle revealed the unstained cellular clusters. Magnified microscopic images of 3R and 7R condyles showed the chondrocyte formation in the cartilage zones, with staining being more intense around regions of chondrocyte-like cells in some areas. Control=The defect with no implanted material, PHA=5% pentanoate-functionalized hyaluronic acid+5% hyaluronic acid nanoparticles, PHA+ RGD and PHA+SP are as for FIG. 1. The text under each staining represent rabbit number and knee side. (e.g., 1R=Rabbit one, right knee) The arrows are pointed at the edges of the defects. Scale bars=1 mm.

In the control group, collagen II staining was prevalent with intensity similar to the surrounding cartilage tissue for the 2R and 3L condyles. In the rest of the control group condyles, the collagen II immunostaining did not cover the whole cartilage region of the regenerated tissue. The 1L and 10L condyles had some staining at the edges of the defects. In the 11R condyle, the staining was not observed at the cartilage surface, and the 12L condyle had mild staining at parts of the cartilage-bone border (FIG. 14). Furthermore, closer observation indicated that in the 2R and 3L condyles, columnar lacunae formations were observed, although in the cartilage zone of the 3L condyle, several fibrocartilage cells clusters were observed where no collagen II staining was present (FIG. 15).

For the PHA group, the collagen II staining was slight in the defect areas of the 1R, 5R, and 8R condyles, and the staining in the 10R, 7L, and 4L condyles was observed at the edges of the defects (FIG. 14). In addition, the 4L condyle had a small patch of collagen II staining in the middle of the defect. Closer observation of the defects indicated that the regenerated tissues of the 5R and 8R condyles had some lacunae in the defect site, but with a poor cartilage and bone structure (FIG. 15). All the defects of the PHA+RGD group had non-prevalent collagen II staining, although the stained regions of the 8L and 9R condyles had the same stain intensity as their surrounding healthy cartilage. The collagen II immunostaining in the 5L and 11L condyles was present at the edges of the defects but not in the center, and staining in the 6R condyle was only observed in the cartilage-bone boarder. For the 2L, 8L, and 9R condyles, no staining was observed at the cartilage surface.

The most prevalent collagen II immunostaining was in the PHA+SP group. From this PHA+SP group, the 3R, 7R, and 9L condyles especially had prevalent collagen II staining, and the intensities were the same as the surrounding cartilage. Staining in the 6L and 12R condyles was only observed in the cartilage-bone border and at the center of the regenerated tissue, respectively. The 4R condyle staining was observed as a small patch in the middle of the defect. Closer observation of the defects (FIG. 15) indicated that the lacunae of the 3R and 7R condyles had some columnar formations but not in all the defect region. The staining for the 7R condyle was intense around several clustered columnar lacunae (FIG. 15).

SPPEPS (SEQ ID NO: 2) Outperforms TGF-β3 in Chondrogenesis

Figure 16:
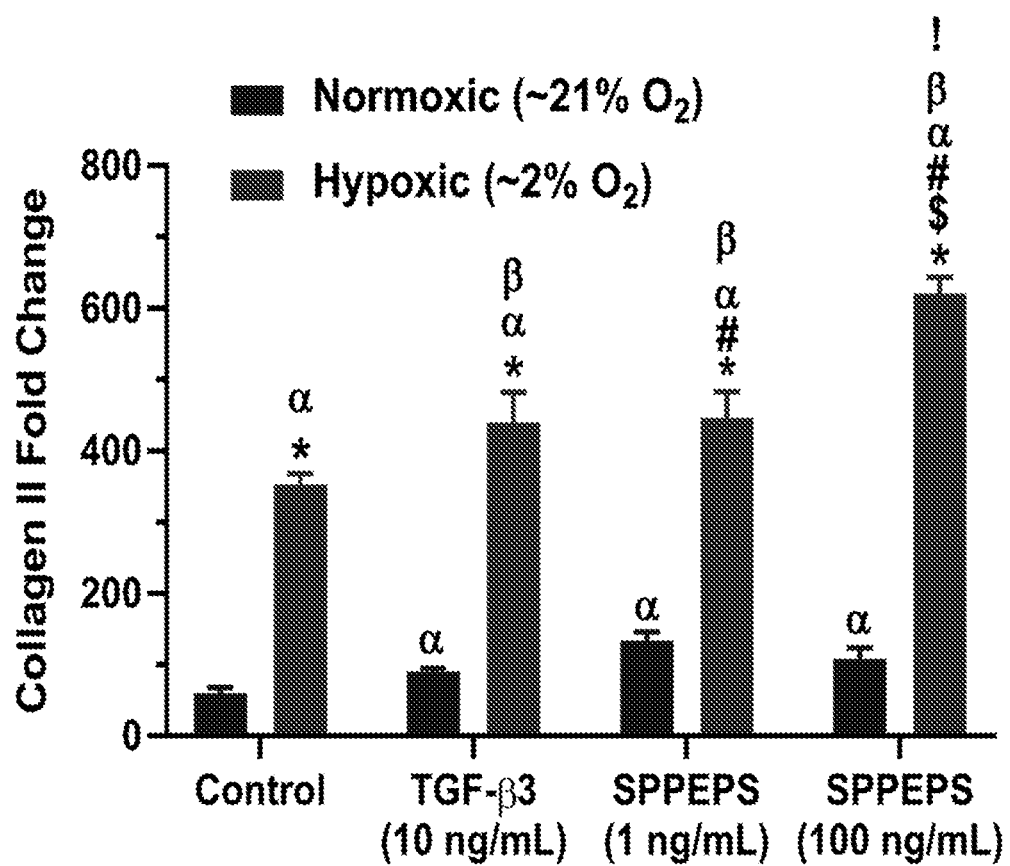
FIG. 16 shows that SPPEPS (SEQ ID NO:2) outperforms TGF-β3 in chondroinduction of rBMSC spheroids at levels of 100 ng/ml SPPEPS. Collagen II gene expression with control (no supplement), TGF-β3, or SPPEPS (1, 100 ng/ml). Hypoxic bars are righthand, normoxic bars are lefthand. n=5, $p<0.05$ difference from αnormoxic control, βhypoxic control, *normoxic counterpart, SSPPEPS (SEQ ID NO: 2) 1 ng/ml, #normoxic TGF-β3,!all groups.

Work disclosed herein demonstrated that SPPEPS (SEQ ID NO:2) upregulated genes associated with chondrogenesis in vitro, with proteomic analyses identifying common upregulated pathways with TGF-β3. RGD and SPPEPS (SEQ ID NO:2) had a powerful synergistic effect with an order of magnitude greater collagen II gene expression by MSCs compared to either peptide alone. In an in vivo study, pentenoate-modified hyaluronic acid (PHA) hydrogels with SPPEPS (SEQ ID NO:2) led to strong collagen II immunostaining 12 weeks after implantation in rabbit medial femoral condyle defects, with visible early column-like clusters of chondrocyte-like cells in lacunae. Thus, PHA plus SPPEPS (SEQ ID NO:2) leads to hyaline-like cartilage that is functionally comparable to healthy native cartilage. The chondroinductivity of SPPEPS (SEQ ID NO:2) was compared to that of TGF-β3 and SPPEPS (SEQ ID NO:2) was shown to outperform TGF-β3 in chondroinduction at a concentration of 100 ng/ml of SPPEPS (SEQ ID NO: 2), as shown in FIG. 16.

Discussion

The work disclosed herein is the first demonstration of chondroinductivity in vivo by conjugating/immobilizing a peptide sequence to a biomaterial implant for cartilage regeneration. A hyaline-like tissue was formed without using exogenous cells, growth factors, or human/animal-derived extracellular matrix.

Incorporation of the peptides into a PHA scaffold elevated the structural integrity of the regenerated cartilage compared to a PHA control group. A significant finding was the superior collagen II production in the PHA+SP group relative to the PHA+RGD group, which was likely due to the fact that although RGD encourages cellular adhesion, it does not provide any chondrogenic-specific signal in the absence of chondrogenic growth factors. Creating true, functional hyaline cartilage has been an elusive goal of cartilage regeneration community. There have been a few approaches in the literature that have evaluated a hyaline-like tissue regeneration by showing superior collagen II IHC staining of the treated groups compared to the non-treated groups in rabbit models. Incorporation of cells in cartilage regeneration approaches has shown promising results and might be useful for treatments of large cartilage defects; however, the translational limitations of cell-based therapies such as high cost, the need for two separate surgeries, and regulatory challenges have inspired the biomaterials community to develop alternative strategies. Employing chondroinductive growth factors in cartilage regeneration approaches would be advantageous to overcome the cell-based therapy limitations and the clinical approval of the number of growth factor based products demonstrate a significant step for overcoming their regulatory barriers. However, the drawbacks associated with growth factors—in addition to their high cost and the associated regulatory classification as a combination product—is their potential for eliciting ectopic tissue formation in vivo. In addition, their short half-life suggests that they need a carrier system to enhance their tissue regeneration potential. The bottom line is that growth factor inclusion, with all translational risks aside, still requires the design of a delivery system that ensures targeted and on demand delivery of the therapeutic is necessary.

In non-limiting embodiments, the present disclosure is therefore directed to:

Clause 1. A chondroinductive composition, comprising: a polymer scaffold, and a peptide comprising an amino acid sequence $X_1$-$X_2$-$X_3$-$X_4$-$X_5$-$X_6$ (SEQ ID NO:1), wherein $X_1$ and $X_6$ are independently selected from serine and threonine; $X_2$, $X_3$ and $X_5$ are independently selected from proline, 3-hydroxyproline, and 4-hydroxyproline; and $X_4$ is glutamic acid or aspartic acid; and wherein the peptide comprises 6 to 50 amino acids.

Clause 2. The chondroinductive composition of clause 1, wherein SEQ ID NO:1 is further defined as the amino acid sequence SPPEPS (SEQ ID NO:2).

Clause 3. The chondroinductive composition of either of clauses 1 or 2, wherein the polymer scaffold is functionalized.

Clause 4. The chondroinductive composition of any one of clauses 1 to 3, wherein the peptide is conjugated to the polymer scaffold.

Clause 5. The chondroinductive composition of any one of clauses 1 to 4, wherein the peptide is conjugated to the polymer scaffold via a linker peptide.

Clause 6. The chondroinductive composition of any one of clauses 1 to 5, wherein the polymer scaffold is a hydrogel.

Clause 7. The chondroinductive composition of any one of clauses 1 to 6, wherein the polymer scaffold comprises hyaluronic acid.

Clause 8. The chondroinductive composition of any one of clauses 1 to 7, wherein the polymer scaffold comprises pentenoate-functionalized hyaluronic acid.

Clause 9. The chondroinductive composition of any one of clauses 1 to 8, wherein the polymer scaffold is coated with the peptide comprising SEQ ID NO:1.

Clause 10. The chondroinductive composition of any one of clauses 1 to 9, wherein the polymer scaffold at least partially encapsulates the peptide comprising SEQ ID NO:1.

Clause 11. The chondroinductive composition of any one of clauses 1 to 10, wherein the polymer scaffold comprises microspheres.

Clause 12. The chondroinductive composition of any one of clauses 1 to 11, further comprising a cell adhesion peptide conjugated to the polymer scaffold.

Clause 13. The chondroinductive composition of clause 12, wherein the cell adhesion peptide is conjugated to the polymer scaffold via a linker molecule.

Clause 14. A peptide, comprising an amino acid sequence $X_1$-$X_2$-$X_3$-$X_4$-$X_5$-$X_6$ (SEQ ID NO:1), wherein $X_1$ and $X_6$ are independently selected from serine and threonine; $X_2$, $X_3$ and $X_5$ are independently selected from proline, 3-hydroxyproline, and 4-hydroxyproline; and $X_4$ is glutamic acid or aspartic acid; and wherein the peptide consists of 6 to 50 amino acids.

Clause 15. The peptide of clause 14, wherein SEQ ID NO:1 is further defined as the amino acid sequence SPPEPS (SEQ ID NO:2).

Clause 16. A peptide compound, comprising (1) a first peptide comprising an amino acid sequence $X_1$-$X_2$-$X_3$-$X_4$-$X_5$-$X_6$ (SEQ ID NO:1), wherein $X_1$ and $X_6$ are independently selected from serine and threonine; $X_2$, $X_3$ and $X_5$ are independently selected from proline, 3-hydroxyproline, and 4-hydroxyproline; and $X_4$ is glutamic acid or aspartic acid; and wherein the peptide comprises 6 to 50 amino acids, and (2) a heterologous linker peptide comprising from 2 to 25 amino acids.

Clause 17. The peptide compound of clause 16, wherein SEQ ID NO:1 is further defined as the amino acid sequence SPPEPS (SEQ ID NO:2).

Clause 18. The peptide compound of either clauses 16 or 17, wherein the heterologous linker peptide extends from either the N-terminal or C-terminal end of the first peptide.

Clause 19. A method of treating a site of a cartilage injury or defect or joint condition in a subject in need of such therapy, comprising administering to the site of the cartilage injury or defect or joint condition a peptide comprising an amino acid sequence $X_1$-$X_2$-$X_3$-$X_4$-$X_5$-$X_6$ (SEQ ID NO:1), wherein $X_1$ and $X_6$ are independently selected from serine and threonine; $X_2$, $X_3$ and $X_5$ are independently selected from proline, 3-hydroxyproline, and 4-hydroxyproline; and $X_4$ is glutamic acid or aspartic acid; and wherein the peptide comprises 6 to 50 amino acids.

Clause 20. The method of clause 19, wherein SEQ ID NO:1 is further defined as the amino acid sequence SPPEPS (SEQ ID NO:2).

Clause 21. The method of either clause 19 or 20, wherein the peptide is linked to a polymer scaffold.

Clause 22. The method of clause 21, wherein the polymer scaffold comprises pentenoate-functionalized hyaluronic acid.

Clause 23. The method of any one of clauses 19-22, wherein the site of the cartilage injury or defect or joint condition is selected from the group consisting of a knee, ankle, wrist, shoulder, elbow, patella, hip, vertebrae, femoral head, temporomandibular joint, glenoid of the scapula, jaw, and growth plate.

Clause 24. A chondroinductive composition or peptide for use in treating a site of a cartilage injury or defect or joint condition in a subject in need of such therapy by administering the chondroinductive composition or peptide of any one of clauses 1 to 18 to the site of the cartilage injury or defect or joint condition.

Clause 25. The chondroinductive composition or peptide of clause 24, wherein the site of the cartilage injury or defect or joint condition is selected from the group consisting of a knee, ankle, wrist, shoulder, elbow, patella, hip, vertebrae, femoral head, temporomandibular joint, glenoid of the scapula, jaw, and growth plate.

Clause 26. A method of treating a site of a cartilage injury or defect or joint condition in a subject in need of such therapy, comprising administering to the site of the cartilage injury or defect or joint condition the chondroinductive composition or peptide of any one of clauses 1 to 18.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

What is claimed is:

1. A chondroinductive composition, comprising: (a) a polymer scaffold, (b) a cell adhesion peptide linked to the polymer scaffold, and (c) a chondroinductive peptide linked to the polymer scaffold, wherein the chondroinductive peptide consists of a linker and an amino acid sequence $X_1$-$X_2$-$X_3$-$X_4$-$X_5$-$X_6$ (SEQ ID NO: 1), wherein the linker extends from the polymer scaffold to the N-terminal end of X1 and consists of 1 to 44 amino acids, and wherein X1 and $X_6$ are independently selected from threonine and serine; $X_2$, $X_3$ and $X_5$ are independently selected from proline, 3-hydroxyproline, and 4-hydroxyproline; and $X_4$ is glutamic acid or aspartic acid.

2. The chondroinductive composition of claim 1, wherein $X_1$ and $X_6$ are serine, $X_2$, $X_3$, and $X_5$ are proline, and $X_4$ is glutamic acid (SEQ ID NO: 2).

3. The chondroinductive composition of claim 1, wherein the polymer scaffold is functionalized.

4. The chondroinductive composition of claim 1, wherein the cell adhesion peptide is an RGD peptide.

5. The chondroinductive composition of claim 1, wherein the polymer scaffold is a hydrogel.

6. The chondroinductive composition of claim 1, wherein the polymer scaffold comprises hyaluronic acid.

7. The chondroinductive composition of claim 1, wherein the polymer scaffold comprises pentenoate-functionalized hyaluronic acid.

8. The chondroinductive composition of claim 1, wherein the polymer scaffold comprises microspheres.

9. The chondroinductive composition of claim 1, wherein the cell adhesion peptide is selected from the group consisting of RGD, LRE, and peptides having amino acid sequences selected from the group consisting of SEQ ID NOS: 3, 6, and 10-67.

10. A method of treating a site of a cartilage injury or defect or joint condition in a subject in need of such therapy, comprising administering to the site of the cartilage injury or defect or joint condition a chondroinductive composition, comprising: (a) a polymer scaffold, (b) a cell adhesion peptide linked to the polymer scaffold, and (c) a chondroinductive peptide linked to the polymer scaffold, wherein the chondroinductive peptide consists of a linker and an amino acid sequence $X_1$-$X_2$-$X_3$-$X_4$-$X_5$-$X_6$ (SEQ ID NO:1), wherein the linker extends from the polymer scaffold to the N-terminal end of X1 and consists of 1 to 44 amino acids, and wherein X1 and X6 are independently selected from threonine and serine, X2, X3 and X5 are independently selected from proline, 3-hydroxyproline, and 4-hydroxyproline, and X4 is glutamic acid or aspartic acid.

11. The method of claim 10, wherein $X_1$ and $X_6$ are serine, $X_2$, $X_3$, and $X_5$ are proline, and $X_4$ is glutamic acid (SEQ ID NO: 2).

12. The method of claim 10, wherein the polymer scaffold comprises pentenoate-functionalized hyaluronic acid.

13. The method of claim 10, wherein the polymer scaffold is a hydrogel.

14. The method of claim 10, wherein the polymer scaffold comprises hyaluronic acid.

15. The method of claim 10, wherein the cell adhesion peptide is an RGD peptide.

16. The method of claim 10, wherein the cell adhesion peptide is selected from the group consisting of RGD, LRE, and peptides having amino acid sequences selected from the group consisting of SEQ ID NOS: 3, 6, and 10-67.

* * * * *

SEQUENCE LISTING

<160> NUMBER OF SEQ ID NOS: 66

<210> SEQ ID NO 1
<211> LENGTH: 6
<212> TYPE: PRT
<213> ORGANISM: Artificial Sequence

```
<220> FEATURE:
<223> OTHER INFORMATION: Completely synthesized in the lab.
<220> FEATURE:
<221> NAME/KEY: misc_feature
<222> LOCATION: (1)..(1)
<223> OTHER INFORMATION: Ser or Thr
<220> FEATURE:
<221> NAME/KEY: misc_feature
<222> LOCATION: (2)..(2)
<223> OTHER INFORMATION: Pro, 3Hyp, or 4Hyp
<220> FEATURE:
<221> NAME/KEY: misc_feature
<222> LOCATION: (3)..(3)
<223> OTHER INFORMATION: Pro, 3Hyp, or 4Hyp
<220> FEATURE:
<221> NAME/KEY: misc_feature
<222> LOCATION: (4)..(4)
<223> OTHER INFORMATION: Glu or Asp
<220> FEATURE:
<221> NAME/KEY: misc_feature
<222> LOCATION: (5)..(5)
<223> OTHER INFORMATION: Pro, 3Hyp, or 4Hyp
<220> FEATURE:
<221> NAME/KEY: misc_feature
<222> LOCATION: (6)..(6)
<223> OTHER INFORMATION: Ser or Thr

<400> SEQUENCE: 1

Xaa Xaa Xaa Xaa Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 2

Ser Pro Pro Glu Pro Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 3

Arg Gly Asp Ser Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 4

Gly Cys Gly Tyr Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Completely synthesized in the lab.
```

```
<400> SEQUENCE: 5

Pro Ser Glu Pro Ser Pro
1               5

<210> SEQ ID NO 6
<211> LENGTH: 10
<212> TYPE: PRT
<213> ORGANISM: Artificial Sequence
<220> FEATURE:
<223> OTHER INFORMATION: Completely synthesized in the lab.

<400> SEQUENCE: 6

Gly Cys Gly Tyr Gly Arg Gly Asp Ser Pro
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Completely synthesized in the lab.

<400> SEQUENCE: 7

Gly Cys Gly Tyr Gly Ser Pro Pro Glu Pro Ser
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Completely synthesized in the lab.

<400> SEQUENCE: 8

Gly Cys Gly Tyr Gly Pro Ser Glu Pro Ser Pro
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Completely synthesized in the lab.

<400> SEQUENCE: 9

Asp His Leu Ser Asp Asn Tyr Thr Leu Asp His Asp Arg Ala Ile His
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 10

Gly Arg Gly Asp Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 11
```

Gly Arg Gly Asp Asn Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 12

Gly Arg Gly Asp Thr Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Completely synthesized in the lab.

<400> SEQUENCE: 13

Gly Arg Gly Asp Ser Pro Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Completely synthesized in the lab.

<400> SEQUENCE: 14

Arg Gly Asp Ser Pro Ala Ser Ser Lys Pro
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Completely synthesized in the lab.

<400> SEQUENCE: 15

Cys Gly Gly Asn Gly Glu Pro Arg Gly Asp Thr Tyr Arg Ala Tyr
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Completely synthesized in the lab.

<400> SEQUENCE: 16

Cys Gly Gly Asn Arg Trp His Ser Ile Tyr Ile Thr Arg Phe Gly
1               5                   10                  15

<210> SEQ ID NO 17
<211> LENGTH: 11
<212> TYPE: PRT
<213> ORGANISM: Artificial Sequence
<220> FEATURE:
<223> OTHER INFORMATION: Completely synthesized in the lab.

<400> SEQUENCE: 17

-continued

```
Cys Gly Gly Glu Ile Leu Asp Val Pro Ser Thr
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Completely synthesized in the lab.

<400> SEQUENCE: 18

Cys Gly Gly Arg Lys Arg Leu Gln Val Gln Leu Ser Ile Arg Thr
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Completely synthesized in the lab.

<400> SEQUENCE: 19

Cys Gly Gly Lys Ala Phe Asp Ile Thr Tyr Val Arg Leu Lys Phe
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Completely synthesized in the lab.

<400> SEQUENCE: 20

Arg Asn Ile Ala Glu Ile Ile Lys Asp Ile Gly Cys
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Completely synthesized in the lab.

<400> SEQUENCE: 21

Cys Gly Gly Val Ser Trp Phe Ser Arg His Arg Tyr Ser Pro Phe Ala
1               5                   10                  15

Val Ser

<210> SEQ ID NO 22
<211> LENGTH: 6
<212> TYPE: PRT
<213> ORGANISM: Artificial Sequence
<220> FEATURE:
<223> OTHER INFORMATION: Completely synthesized in the lab.
<220> FEATURE:
<221> NAME/KEY: misc_feature
<222> LOCATION: (3)..(3)
<223> OTHER INFORMATION: Xaa is hydroxyproline.

<400> SEQUENCE: 22

Gly Phe Xaa Gly Glu Arg
1               5

<210> SEQ ID NO 23
<211> LENGTH: 4
<212> TYPE: PRT
<213> ORGANISM: Artificial Sequence
```

```
<220> FEATURE:
<223> OTHER INFORMATION: Completely synthesized in the lab.

<400> SEQUENCE: 23

Asp Gly Glu Ala
1

<210> SEQ ID NO 24
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 24

Tyr Ile Gly Ser Arg
1               5

<210> SEQ ID NO 25
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 25

Tyr Ile Gly Ser Arg
1               5

<210> SEQ ID NO 26
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 26

Ser Ile Lys Val Ala Val
1               5

<210> SEQ ID NO 27
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 27

Ile Lys Val Ala Val
1               5

<210> SEQ ID NO 28
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 28

Ile Lys Leu Leu Ile
1               5

<210> SEQ ID NO 29
<211> LENGTH: 5
<212> TYPE: PRT
<213> ORGANISM: Artificial Sequence
<220> FEATURE:
```

```
<223> OTHER INFORMATION: Completely synthesized in the lab.

<400> SEQUENCE: 29

Leu Arg Gly Asp Asn
1               5

<210> SEQ ID NO 30
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 30

Ser Ile Asn Asn Asn Arg
1               5

<210> SEQ ID NO 31
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 31

Pro Asp Gly Ser Arg
1               5

<210> SEQ ID NO 32
<211> LENGTH: 11
<212> TYPE: PRT
<213> ORGANISM: Artificial Sequence
<220> FEATURE:
<223> OTHER INFORMATION: Completely synthesized in the lab.

<400> SEQUENCE: 32

Gly Thr Phe Ala Leu Arg Gly Asp Asn Gly Gln
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Completely synthesized in the lab.

<400> SEQUENCE: 33

Cys Phe Ala Leu Arg Gly Asp Asn Pro
1               5

<210> SEQ ID NO 34
<211> LENGTH: 12
<212> TYPE: PRT
<213> ORGANISM: Artificial Sequence
<220> FEATURE:
<223> OTHER INFORMATION: Completely synthesized in the lab.

<400> SEQUENCE: 34

Asn Pro Trp His Ser Ile Tyr Ile Thr Arg Phe Gly
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Completely synthesized in the lab.
```

```
<400> SEQUENCE: 35

Thr Trp Tyr Lys Ile Ala Phe Gln Arg Asn Arg Lys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Completely synthesized in the lab.

<400> SEQUENCE: 36

Lys Ala Phe Asp Ile Thr Tyr Val Arg Leu Lys Phe
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 37

Leu Gly Thr Ile Pro Gly
1               5

<210> SEQ ID NO 38
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 38

Pro Lys Arg Gly Asp Leu
1               5

<210> SEQ ID NO 39
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 39

Asn Gly Arg Ala His Ala
1               5

<210> SEQ ID NO 40
<211> LENGTH: 10
<212> TYPE: PRT
<213> ORGANISM: Artificial Sequence
<220> FEATURE:
<223> OTHER INFORMATION: Completely synthesized in the lab.

<400> SEQUENCE: 40

Gly Ala Cys Arg Gly Asp Cys Leu Gly Ala
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Completely synthesized in the lab.
```

```
<400> SEQUENCE: 41

Ile Asp Ala Pro Ser
1               5

<210> SEQ ID NO 42
<211> LENGTH: 4
<212> TYPE: PRT
<213> ORGANISM: Artificial Sequence
<220> FEATURE:
<223> OTHER INFORMATION: Completely synthesized in the lab.

<400> SEQUENCE: 42

Arg Glu Asp Val
1

<210> SEQ ID NO 43
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 43

Pro His Ser Arg Asn
1               5

<210> SEQ ID NO 44
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 44

Lys Gln Ala Gly Asp Val
1               5

<210> SEQ ID NO 45
<211> LENGTH: 8
<212> TYPE: PRT
<213> ORGANISM: Artificial Sequence
<220> FEATURE:
<223> OTHER INFORMATION: Completely synthesized in the lab.

<400> SEQUENCE: 45

Trp Gln Pro Pro Arg Ala Arg Ile
1               5

<210> SEQ ID NO 46
<211> LENGTH: 8
<212> TYPE: PRT
<213> ORGANISM: Artificial Sequence
<220> FEATURE:
<223> OTHER INFORMATION: Completely synthesized in the lab.

<400> SEQUENCE: 46

Ser Pro Pro Arg Arg Ala Arg Val
1               5

<210> SEQ ID NO 47
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 47
```

```
Leu Ile Gly Arg Lys Lys
1               5
```

<210> SEQ ID NO 48
<211> LENGTH: 19
<212> TYPE: PRT
<213> ORGANISM: Artificial Sequence
<220> FEATURE:
<223> OTHER INFORMATION: Completely synthesized in the lab.

<400> SEQUENCE: 48

```
Ile Trp Lys His Lys Gly Arg Asp Val Ile Leu Lys Lys Asp Val Arg
1               5                   10                  15

Phe Tyr Cys
```

<210> SEQ ID NO 49
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 49

```
Lys Leu Asp Ala Pro
1               5
```

<210> SEQ ID NO 50
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 50

```
Pro Arg Ala Arg Ile
1               5
```

<210> SEQ ID NO 51
<211> LENGTH: 13
<212> TYPE: PRT
<213> ORGANISM: Artificial Sequence
<220> FEATURE:
<223> OTHER INFORMATION: Completely synthesized in the lab.

<400> SEQUENCE: 51

```
Cys Lys Lys Gln Arg Phe Arg His Arg Asn Arg Lys Gly
1               5                   10
```

<210> SEQ ID NO 52
<211> LENGTH: 4
<212> TYPE: PRT
<213> ORGANISM: Artificial Sequence
<220> FEATURE:
<223> OTHER INFORMATION: Completely synthesized in the lab.

<400> SEQUENCE: 52

```
Lys Arg Ser Arg
1
```

<210> SEQ ID NO 53
<211> LENGTH: 7
<212> TYPE: PRT
<213> ORGANISM: Artificial Sequence
<220> FEATURE:
<223> OTHER INFORMATION: Completely synthesized in the lab.

```
<400> SEQUENCE: 53

Phe His Arg Arg Ile Lys Ala
1               5

<210> SEQ ID NO 54
<211> LENGTH: 7
<212> TYPE: PRT
<213> ORGANISM: Artificial Sequence
<220> FEATURE:
<223> OTHER INFORMATION: Completely synthesized in the lab.

<400> SEQUENCE: 54

Ser Val Val Tyr Gly Leu Arg
1               5

<210> SEQ ID NO 55
<211> LENGTH: 13
<212> TYPE: PRT
<213> ORGANISM: Artificial Sequence
<220> FEATURE:
<223> OTHER INFORMATION: Completely synthesized in the lab.

<400> SEQUENCE: 55

Glu Leu Val Thr Asp Phe Pro Thr Asp Leu Pro Ala Thr
1               5                   10

<210> SEQ ID NO 56
<211> LENGTH: 5
<212> TYPE: PRT
<213> ORGANISM: Artificial Sequence
<220> FEATURE:
<223> OTHER INFORMATION: Completely synthesized in the lab.

<400> SEQUENCE: 56

Val Pro Gly Ile Gly
1               5

<210> SEQ ID NO 57
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 57

Val Gly Val Ala Pro Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Completely synthesized in the lab.

<400> SEQUENCE: 58

Cys Asn Tyr Tyr Ser Asn Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Completely synthesized in the lab.

<400> SEQUENCE: 59
```

```
Met Asn Tyr Tyr Ser Asn Ser
1               5

<210> SEQ ID NO 60
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 60

Cys Ser Val Thr Cys Gly
1               5

<210> SEQ ID NO 61
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 61

Gly Arg Gly Asp Ala Cys
1               5

<210> SEQ ID NO 62
<211> LENGTH: 12
<212> TYPE: PRT
<213> ORGANISM: Artificial Sequence
<220> FEATURE:
<223> OTHER INFORMATION: Completely synthesized in the lab.

<400> SEQUENCE: 62

Phe Gln Gly Val Leu Gln Asn Val Arg Phe Val Phe
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 63

Ala Glu Leu Asp Val Pro
1               5

<210> SEQ ID NO 64
<211> LENGTH: 6
<212> TYPE: PRT
<213> ORGANISM: Artificial Sequence
<220> FEATURE:
<223> OTHER INFORMATION: Completely synthesized in the lab.

<400> SEQUENCE: 64

Val Ala Leu Asp Glu Pro
1               5

<210> SEQ ID NO 65
<211> LENGTH: 7
<212> TYPE: PRT
<213> ORGANISM: Artificial Sequence
<220> FEATURE:
<223> OTHER INFORMATION: Completely synthesized in the lab.

<400> SEQUENCE: 65
```

```
Gly Phe Arg Gly Asp Gly Gln
1               5

<210> SEQ ID NO 66
<211> LENGTH: 11
<212> TYPE: PRT
<213> ORGANISM: Artificial Sequence
<220> FEATURE:
<223> OTHER INFORMATION: Completely synthesized in the lab.

<400> SEQUENCE: 66

Ser Ile Gly Phe Arg Gly Asp Gly Gln Thr Cys
1               5                   10
```